(12) United States Patent
Li et al.

(10) Patent No.: US 9,724,022 B2
(45) Date of Patent: *Aug. 8, 2017

(54) APPARATUS FOR NON-INVASIVE GLUCOSE MONITORING

(71) Applicant: Taiwan Biophotonic Corporation, Hsinchu (TW)

(72) Inventors: Yu-Tang Li, New Taipei (TW); Chang-Sheng Chu, Hsinchu (TW); Chih-Hsun Fan, Hsinchu (TW); Shuang-Chao Chung, Hsinchu County (TW); Ming-Chia Li, Taichung (TW); Jyh-Chern Chen, New Taipei (TW); Kuo-Tung Tiao, Hsinchu County (TW)

(73) Assignee: Taiwan Biophotonic Corporation, Hsinchu (TW)

( * ) Notice: Subject to any disclaimer, the term of this patent is extended or adjusted under 35 U.S.C. 154(b) by 136 days.

This patent is subject to a terminal disclaimer.

(21) Appl. No.: 14/141,459

(22) Filed: Dec. 27, 2013

(65) Prior Publication Data

US 2014/0171765 A1      Jun. 19, 2014

Related U.S. Application Data

(63) Continuation-in-part of application No. 13/457,517, filed on Apr. 27, 2012.

(Continued)

(30) Foreign Application Priority Data

Dec. 5, 2013  (TW) .............................. 102144645 A

(51) Int. Cl.
| A61B 5/1455 | (2006.01) |
| A61B 5/145  | (2006.01) |
| A61B 3/00   | (2006.01) |

(52) U.S. Cl.
CPC ........ *A61B 5/14532* (2013.01); *A61B 3/0008* (2013.01); *A61B 3/0025* (2013.01); *A61B 5/14558* (2013.01)

(58) Field of Classification Search
CPC . A61B 5/0059; A61B 5/1455; A61B 5/14551; A61B 5/14552; A61B 5/14532;
(Continued)

(56) References Cited

U.S. PATENT DOCUMENTS 3,958,560 A    5/1976  March
5,348,003 A *  9/1994  Caro .................... A61B 5/1455
                                                        600/310
(Continued)

FOREIGN PATENT DOCUMENTS

CN       201379553 Y     1/2010
EP       0589191         3/1994
(Continued)

OTHER PUBLICATIONS

Wolfgang Schrader et al., "Non-invasive glucose determination in the human eye", Journal of Molecular Sructure, Feb. 2005, p. 299-p. 306.
(Continued)

*Primary Examiner* — Eric Winakur
*Assistant Examiner* — Chu Chuan (JJ) Liu
(74) *Attorney, Agent, or Firm* — Steven Reiss

(57) ABSTRACT

An apparatus for non-invasive glucose monitoring includes a light source for emitting at least one ray of light; a first beam splitter, a set of photo detectors for measuring optical rotatory distribution (ORD) information and absorption energy information; a reference component receiving the light from the first beam splitter, and the light reflected by the reference component being transmitted to the set of photo detectors by the first beam splitter, wherein the light
(Continued)

emitted from the light source is transmitted to the set of photo detectors by the first beam splitter and the eyeball to form a first optical path, the light emitted from the light source is transmitted to the set of photo detectors by the first beam splitter and the reference component to form a second optical path; and a processing unit receiving and processing the ORD information and the absorption energy information to obtain a glucose information.

20 Claims, 15 Drawing Sheets

Related U.S. Application Data

(60) Provisional application No. 61/746,576, filed on Dec. 28, 2012, provisional application No. 61/480,386, filed on Apr. 29, 2011, provisional application No. 61/508,078, filed on Jul. 15, 2011.

(58) Field of Classification Search
CPC .. A61B 5/145; A61B 5/14555; A61B 5/14558
USPC ....... 600/310, 318, 319, 316, 322, 336, 340, 600/473, 476
See application file for complete search history.

(56) References Cited

U.S. PATENT DOCUMENTS

| | | | |
|---|---|---|---|
| 5,433,197 A | 7/1995 | Stark | |
| 5,535,743 A | 7/1996 | Backhaus et al. | |
| 5,820,557 A | 10/1998 | Hattori et al. | |
| 5,835,215 A | 11/1998 | Toida et al. | |
| 5,879,294 A | 3/1999 | Anderson et al. | |
| 6,083,158 A | 7/2000 | Bearman et al. | |
| 6,152,875 A | 11/2000 | Hakamata | |
| 6,166,807 A | 12/2000 | Kawamura et al. | |
| 6,181,957 B1 | 1/2001 | Lambert et al. | |
| 6,226,089 B1 * | 5/2001 | Hakamata | A61B 5/14532 600/319 |
| 6,424,850 B1 | 7/2002 | Lambert et al. | |
| 6,836,337 B2 | 12/2004 | Cornsweet | |
| 6,999,808 B2 | 2/2006 | Gobeli et al. | |
| 7,167,736 B2 | 1/2007 | Winther | |
| 7,245,952 B2 | 7/2007 | Cameron | |
| RE40,316 E | 5/2008 | Gobeli et al. | |
| 7,627,357 B2 | 12/2009 | Zribi et al. | |
| 7,653,424 B2 | 1/2010 | March | |
| 7,769,419 B2 | 8/2010 | Daly | |
| 2003/0233036 A1 | 12/2003 | Ansari et al. | |
| 2008/0269580 A1 | 10/2008 | Balistreri et al. | |
| 2010/0234704 A1 | 9/2010 | Cameron | |
| 2011/0105868 A1 | 5/2011 | Westphal | |

FOREIGN PATENT DOCUMENTS

| | | |
|---|---|---|
| EP | 0589191 A | 3/1994 |
| EP | 2517624 | 10/2012 |
| EP | 2517624 A | 10/2012 |
| WO | 01/22871 A1 | 4/2001 |

OTHER PUBLICATIONS

Wei-Hsiung Wang, "abstract of In Vivo, Non-invasive Glucose Monitoring with Optical Heterodyne Polaimeter", Thesis for Master of Department of Biomedical Imaging and Radiological Sciences, National Yang-Ming University, issued on 2001.

Wang et al., "In Vivo, noninvasive glucose monitoring with optical heterodyne polarimetry in a range of 50 mg/dl-100 mg/dl," Proc. SPIE 4082, Optical Sensing, Imaging, and Manipulation for Biological and Biomedical Applications, Jul. 4, 2000, pp. 192-197.

Kulkarni et al., "A Feasibility Study on Noninvasive Blood Glucose Measurement Using Photoacoustic Method," 4th International Conference on Bioinformatics and Biomedical Engineering (iCBBE), Jun. 18-20, 2010, pp. 1-4.

"Office Action of European Counterpart Application", issued on Mar. 6, 2014, p. 1-p. 6.

Micheal F. G. Wood, "Combined optical intensity and polarization methodology for analyte concentration determination in simulated optically clear and turbid biological media", Journal of Biomedical Optics, Jul./Aug. 2008, pp. 044037-1 to 044037-9, vol. 13(4), International Society for Optical Engineering, US.

* cited by examiner

APPARATUS FOR NON-INVASIVE GLUCOSE MONITORING

CROSS-REFERENCE TO RELATED APPLICATION

This application is a continuation-in-part application of and claims the priority benefit of a prior application Ser. No. 13/457,517, filed on Apr. 27, 2012. The prior application Ser. No. 13/457,517 claims the priority benefit of U.S. provisional application Ser. No. 61/480,386, filed on Apr. 29, 2011, and U.S. provisional application Ser. No. 61/508,078, filed on Jul. 15, 2011. This continuation-in-part application also claims the priority benefits of U.S. provisional application Ser. No. 61/746,576, filed on Dec. 28, 2012, and Taiwan application serial no. 102144645, filed on Dec. 5, 2013. The entirety of each of the above-mentioned patent applications is hereby incorporated by reference herein and made a part of this specification.

TECHNICAL FIELD

The disclosure relates to an apparatus for glucose monitoring, and more particularly to, an apparatus for non-invasive glucose monitoring.

BACKGROUND

Diabetes is a clinical syndrome caused by factors such as absolute or relative lack of insulin in the body, abnormal secretion time, or disorder or resistance of insulin effector, etc. If the diabetes is not suitably controlled, it may cause some acute complications such as hypoglycemia, ketoacidosis, nonketotic hyperosmolar coma, etc. The serious long-term complications include cardiovascular diseases, chronic renal failure, retinopathy, neuropathy and microvascular diseases, etc.

Constant blood glucose monitoring is very important for diabetics. A primary objective of treating the diabetic is to maintain a normal concentration of glucose, and if a patient carefully controls blood glucose daily, occurrence of the above complications may be effectively prevented.

Presently, the diabetic generally use blood glucose monitor to monitor the blood glucose. However, before the blood glucose monitor is used to measure a concentration of blood glucose, blood collection has to be first performed. Fingertip is an invasive (destructive) sampling method for blood collection, and a process thereof is complicated and may cause pain, which is also an important reason why the diabetic cannot periodically monitor the blood glucose.

Therefore, a method for non-invasive blood glucose monitoring becomes a development trend in blood glucose detection. The existing non-invasive glucose meters measure the blood glucose through a single method (for example, an acoustic method, an optical method or an electrical method), though the measurements are mainly performed in allusion to skin blood glucose of human body. However, the skin is composed of epidermis, dermis, subcutaneous tissues, and different tissues, blood vessels and water in the skin may produce scattering light and absorption light, which may influence signal measurement, and accordingly influence the accuracy of measured concentration of blood glucose.

SUMMARY OF THE INVENTION

The disclosure provides an apparatus for non-invasive glucose monitoring capable of measuring a blood glucose information accurately.

The disclosure provides an apparatus for non-invasive glucose monitoring comprising at least one light source, a first beam splitter, a set of photo detectors, a reference component and a processing unit. The light source emits at least one ray of light. The first beam splitter with a focusing function leads the light emitted from the light source into an eyeball and focuses on the eyeball through the first beam splitter. The set of photo detectors measures an optical angular information and an absorption energy information of the light reflected from the eyeball and transmitted through the first beam splitter to the set of photo detectors. The reference component receives the light from the first beam splitter, and the light reflected by the reference component is transmitted to the set of photo detectors by the first beam splitter, wherein the light generated from the light source is transmitted to the set of photo detectors by the first beam splitter and the eyeball to form a first optical path, the light generated from the light source is transmitted to the set of photo detectors by the first beam splitter and the reference device component to form a second optical path. The processing unit receives and processes the optical angular information and the absorption energy information to obtain a glucose information.

In view of foregoing, since the apparatus for non-invasive glucose monitoring provided in the disclosure has the reference component, light intensity difference caused by environmental impact can thus be avoided, so as to obtain a more precise glucose information for enhancing an accuracy of blood glucose information (e.g., concentration of blood glucose) and also for calibrating an opto-element system. In addition, when establishing personal parameters for a user with individual differences, through relationship with the reference component, glucose may be analyzed using data collected during the first lancing, thus no additional lancing is required later.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

The disclosure provides an apparatus for non-invasive glucose monitoring capable of accurately measure a glucose information (e.g., concentration of glucose) of a measuring object, and since the glucose information (e.g., concentration of glucose) in an eyeball (e.g., aqueous humor within eyeball) has a corresponding relationship with a blood glucose information (e.g., concentration of blood glucose), the blood glucose information (e.g., concentration of blood glucose) may be read, through this corresponding relationship, by using the apparatus for non-invasive glucose monitoring of the disclosure to detect the glucose information (e.g., concentration of glucose) in the eyeball (e.g., aqueous humor within the eyeball).

The disclosure also provides a method for non-invasive glucose monitoring to measure concentration of glucose in real time.

Figure 1A:
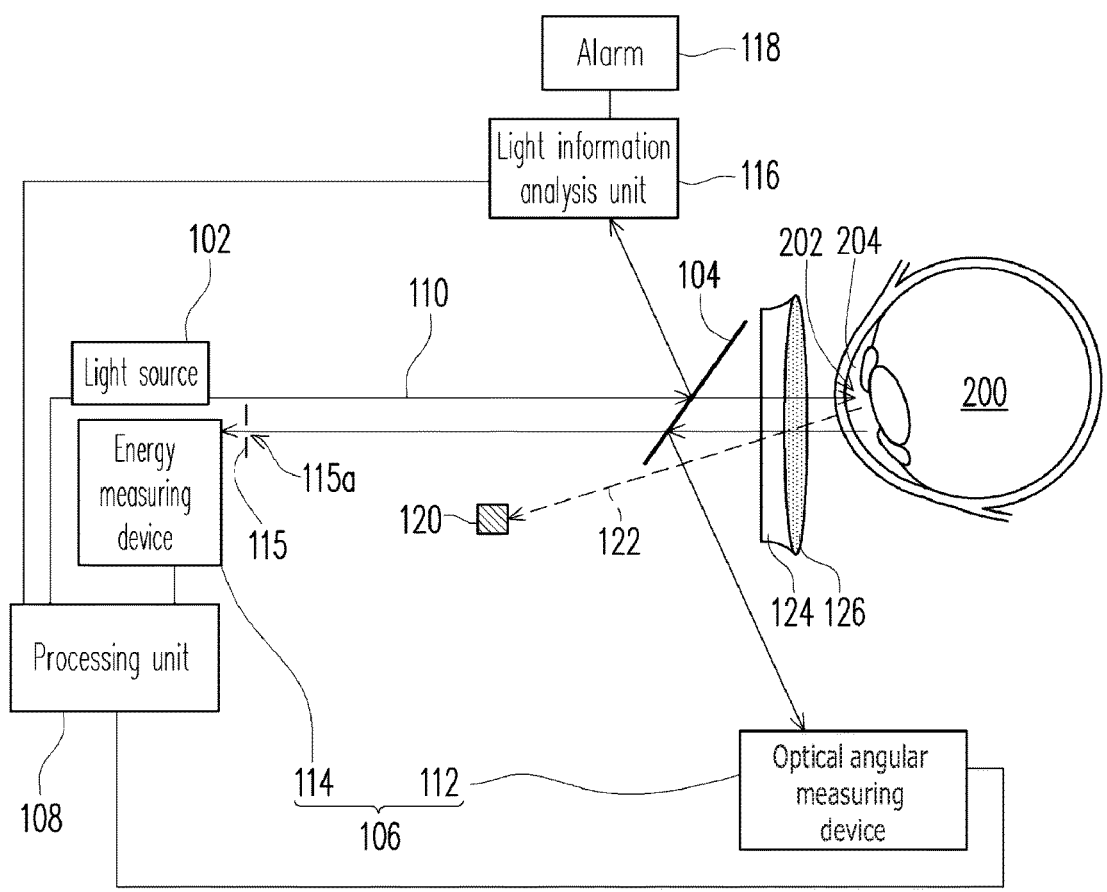
FIG. 1A is a schematic diagram illustrating an apparatus for non-invasive glucose monitoring in accordance with a first exemplary embodiment.
Figure 1B:
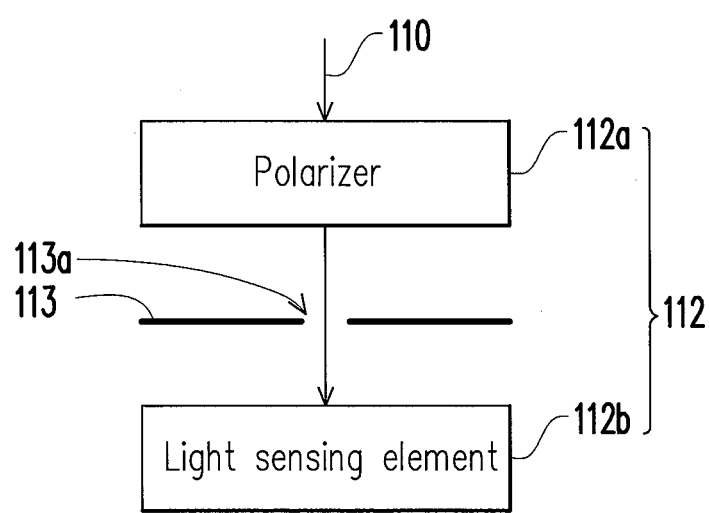
FIG. 1B is a schematic diagram illustrating an optical rotatory distribution measuring device in FIG. 1A.

FIG. 1A is a schematic diagram illustrating an apparatus for non-invasive glucose monitoring in accordance with a first exemplary embodiment. FIG. 1B is a schematic diagram illustrating an optical angular measuring device from FIG. 1A in accordance with the first exemplary embodiment.

With reference to FIG. 1A, an apparatus for non-invasive glucose monitoring 100 which comprises a light source 102, a beam splitter 104, a set of photo detectors 106, and a processing unit 108. The apparatus for non-invasive glucose monitoring 100 may, for example, detect concentration of glucose of an aqueous humor 204 in an anterior chamber 202 of an eyeball 200.

The light source 102 generates at least one ray of light 110. The light source 102 is, for example, a light emitting diode (LED), a laser diode, or other light source. A wavelength of the light source 102 is, for example, which can be absorbed by glucose molecules and namely, a wavelength that is capable of being absorbed by the glucose molecules in the eyeball 200, such as an infrared light. The light 110 emitted from the light source 102 comprises a linear polarized light, a circular polarized light, an elliptical polarized light, or a partial polarized light. Moreover, the light source 102 may have a function for controlling an emitting frequency of the light 110, which avails the photo detector set 106 in determining the light to be measured according to the emitting frequency. In addition, the light source 102 may have a function for controlling an intensity of the light 110, which assures the light entering into the eyeball 200 is unable to cause any harm. Furthermore, the light source 102 may have a function for controlling a length of turn-on time of the light 110 and controlling a length of turn-off time of the light 110, or a combination thereof, which provides a glucose detection time on one hand but also ensures that the light energy entering into the eyeball 200 is unable to cause any harm on the other hand. Although, in the present exemplary embodiment, the single light 110 emitted from the single light source 102 is taken as an example for description, the disclosure is not limited thereto; and, in another exemplary embodiment, types of the light source 102 and types of the light 110 may be two or more.

The beam splitter 104 with a focusing function which can lead the light 110 emitted from the light source 102 into an eyeball 200 and focus on the eyeball 200 through the beam splitter 104. The beam splitter 104 is, for example, focusing the light 110 onto the anterior chamber 202 of the eyeball 200, and the light 110 reflected from the eyeball 200 comprises the reflected light reflected from the aqueous humor 204. The beam splitter 104 is, for example, an optical film, a lens, a grating, a diffractive optic device or a combination of any the above elements.

The set of photo detectors 106 measures an optical angular information and an absorption energy information of the light 110 reflected from the eyeball 200 and then transmitted through the beam splitter 104 to the set of photo detectors 106. In the present exemplary embodiment, the set of photo detectors 106 comprises an optical angular measuring device 112 and an energy measuring device 114. Wherein, the optical angular measuring device 112 is used for measuring the optical angular information of the light 110 reflected from the eyeball 200 and then transmitted through the beam splitter 104, and the energy measuring device 114 is used for measuring the absorption energy information of the light 110 reflected from the eyeball 200 and then passed through the beam splitter 104.

In another exemplary embodiment, the optical angular measuring device 112 and the energy measuring device 114 may be exchanged. Namely, the optical angular measuring device 112 is used to measure the optical angular information of the light 110 reflected from the eyeball 200 and then passed through the beam splitter 104, and the energy measuring device 114 is used to measure the absorption energy information of the light 110 reflected from the eyeball 200 and then reflected by the beam splitter 104.

With reference to FIG. 1B, the optical angular measuring device 112 comprises a polarizer 112a and a light sensing element 112b, wherein the light is firstly passed through the polarizer 112a, and then transmitted to the light sensing element 112b. The optical angular measuring device 112 is, for example, an active optical angular measuring device or a passive optical angular measuring device, wherein a measurement angle of the active optical angular measuring device may be changed whereas a measurement angle of the passive optical angular measuring device is fixed. The active optical angular measuring device is, for example, a polarizer which may directly calculate the optical angular information. The passive optical angular measuring device is to measure the energy of the light 110 that passed through a polarizer 112a using the light sensing element 112b to calculate the angular information of the optical angular information. The energy measuring device 114 is, for example, a light sensing element such as a charge coupled device (CCD), a complementary metal oxide semiconductor sensors or a light emitting diode.

Moreover, with reference to FIGS. 1A and 1B, the apparatus for non-invasive glucose monitoring 100 may further selectively comprise at least one of a light barrier 113 and a light barrier 115. The light barrier 113 has an opening 113a, and the opening 113a, through assembly, may enable the light 110 to pass through the light barrier 113, and then transmit to the light sensing element 112b. The light barrier 113 is, for example, disposed between the polarizer 112a and the light sensing element 112b, but the disclosure is not limited thereto. In another exemplary embodiment, the light barrier 113 may further enable the light 110 to pass through the polarizer 112a and then through the opening 113a of the light barrier 113. In addition, the light barrier 115 has an opening 115a, and the opening 115a, through assembly, may enable the light 110 to pass through the light barrier 115, and then transmit to the energy measuring device (e.g., light sensing element). The light barriers 113, 115 respectively are, for example, a metal photomask or a silica glass photomask. The light barriers 113, 115 respectively may prevent stray light from entering into the optical angular measuring device 112 and the energy measuring device 114, and thus may reduce interference from the stray light, so as to enhance the signal to noise ratio (S/N ratio). It is noted that each of the following exemplary embodiments, through the light barrier, may reduce the influence of stray light on the measurement results of the optical angular measuring device and of the energy measuring device; however, further elaboration on the light barrier in the another exemplary embodiment is omitted in order to simplify the description.

Referring to FIG. 1A again, the processing unit 108 is, for example, coupled to the optical angular measuring device 112 and the energy measuring device 114 of the set of photo detectors 106, and receives and processes the optical angular information and the absorption energy information to obtain an optical angular difference and an absorption energy difference between the light 110 emitted from the light source 102 and the light 110 transmitted to the set of photo detectors 106, and to obtain biological molecule information, which at least comprises a glucose, by analyzing the optical angular difference and the absorption energy difference. The processing unit obtains the glucose information through analyzing the biological molecule information. The biological molecule is, for example, cholesterol, uric acid, water, lactic acid, urea, ascorbic acid, or a combination thereof. Moreover, the biological molecule may comprise one kind of interference molecules therein, and the kind of interference molecule is, for example, one kind of molecule different from the measurement target (e.g., glucose), such as cholesterol, uric acid, water, lactic acid, urea, or ascorbic acid. As ascorbic acid and lactic acid may generate interference onto the optical angular information, whereas water may generate interference to the absorption energy information. During the process of obtaining the glucose information through the processing unit 108, the processing unit 108 may remove interference signals caused by the interference molecules. The processing unit 108 may also control a light quality, an opto-element offset or a combination thereof, and statistically analyze the optical angular information and the absorption energy information, so as to obtain the glucose information. The spatial variation of the light source comprises a light emitting frequency variation, a light energy intensity variation, a length variation of turn-on time of the light, a length variation of turn-off time of the light, or a combination thereof. Since the glucose concentration in the eyeball 200 (e.g., aqueous humor within eyeball) has a corresponding relationship with a blood glucose concentration, the blood glucose information (e.g., concentration of blood glucose) is read, through this corresponding relationship, by using the apparatus for non-invasive glucose monitoring of the disclosure to detect the glucose information (e.g., concentration of glucose) in the eyeball (e.g., aqueous humor within the eyeball). The processing unit 108 is, for example, an analog digital circuit integration module, wherein the analog digital circuit integration module comprises a microprocessor, an amplifier and an analog digital converter (ADC). The analog digital circuit integration module may further comprise a wireless transmission device.

In the present exemplary embodiment, the processing unit 108 is, for example, coupled to the light source 102 to control an optical characteristic of the light 110 emitted from the light source 102.

The apparatus for non-invasive glucose monitoring 100 may selectively comprise a light information analysis unit 116 for detecting a light information of the light 110 from the beam splitter 104 before the light 110 is leaded into the eyeball 200, and selectively transmit the light information of the light 110 to the processing unit 108 or an alarm 118 to perform a feedback control with the optical characteristic of the light 110. The light information analysis unit 116 comprises at least one of an optical power meter and an optical sensor, the light information detected by the optical power meter is energy information whereas the light information detected by the optical sensor is at least one of energy information or position information. The optical characteristic of the light 110 is, for example, energy emittance and/or light position.

When the emitting energy of the light 110 emitted from the light source 102 is excessively high, where the light 110 may cause harm to the eyeball 200. Therefore, when the processing unit 108 receives the energy information indicating excessive emitting energy of the light 110, the processing unit 108 will reduce the emitting energy of the light 110 emitted from the light source 102. On the other hand, when the alarm 118 receives the energy information indicating excessive emitting energy of the light 110, the alarm 118 sends a light or a sound warning signal to notify the user that the emitting energy of the light 110 emitted from the light source 102 is excessively high, and the emitting energy of the light 110 is to be adjusted. Therefore, usage of the light information analysis unit 116 may prevent a condition of harming the eyeball 200 due to excessive emitting energy of the light 110.

Moreover, when the light position of the light 110 emitted from light source 102 is shifted, the accuracy of a glucose measurement is lowered. Therefore, when the processing unit 108 receives the position information indicating the light position of the light 110 is shifted, the processing unit 108 adjusts the light position of the light 110 emitted from the light source 102. On the other hand, when the alarm 118 receives the position information indicating the light position of the light 110 is shifted, the alarm 118 sends the light or the sound warning signal to notify the user that the light position of the light 110 emitted from the light source 102 is shifted, and the light position of the light 110 is to be adjusted. Therefore, usage of the light information analysis unit 116 may prevent the light position of the light 110 from shifting, thus enhancing the accuracy of the glucose measurement.

In the present exemplary embodiment, the energy information detected by the light information analysis unit 116 is simultaneously transmitted to the processing unit 108 and the alarm 118; nevertheless, the feedback control may be implemented as long as the energy information is transmitted to one of the processing unit 108 and the alarm 118. The light information analysis unit 116 is, for example, respectively coupled to the processing unit 108 and the alarm 118, but a coupling manner of the light information analysis unit 116, the processing unit 108 and the alarm 118 is not limited thereto.

In another exemplary embodiment, the light source 102 is, for example, coupled to a light source control unit (not shown), and now the light information analysis unit 116 transmits the energy information of the light 110 to the light source control unit, so as to perform the feedback control for the light source 102.

In addition, before the light 110 is leaded into the eyeball 200, the detection of the light 110 reflected by the beam splitter 104 using the light information analysis unit 116 is taken as an example to describe the present exemplary embodiment.

The apparatus for non-invasive glucose monitoring 100 may further selectively include a reference component 128. The reference component 128 receives the light 110 from the beam splitter 104, and the light 110 reflected by the reference component 128 is transmitted to the set of photo detectors 106 through the beam splitter 104, wherein the light 110 emitted from the light source 102 is transmitted to the set of photo detectors 106 through the beam splitter 104 and the eyeball 200 to form a first optical path, and the light 110 emitted from the light source 102 is transmitted to the set of photo detectors 106 through the beam splitter 104 and the reference component 128 to from a second optical path. As such, environmental impact on the light 110, such as influences to an absorption energy intensity and an optical angular intensity caused by changes in temperature inside and outside the system and noise interference of the circuit itself, may be detected, thereby facilitating in the performance of an internal calibration.

The reference component 128 may be a reference sheet or a reference solution. The reference component 128, for example, is a light absorbing material, a light reflective material or a solution. For instance, the reference component 128 may be a vapor deposition sheet, a light absorption sheet or a standard concentration glucose solution.

The light 110 reflected by the reference component 128 on the second optical path has a characteristic intensity. When performing actual measurements, the set of photo detectors 106 obtains a reference intensity of the light 110 reflected by the reference component 128 from the second optical path. The processing unit 108 may obtain the optical angular difference and the absorption energy difference between the light 110 emitted from the light source 102 and the light 110 transmitted to the set of photo detectors 106 from the first optical path, and a light intensity difference caused by the environmental impact may be avoided by comparing the characteristic intensity and the reference intensity, so that the biological molecule information of the biological molecule is obtained, wherein the biological molecule at least comprises the glucose. The processing unit 108 obtains the glucose information through analyzing the biological molecule information, and since the glucose concentration has a corresponding relationship with the blood glucose concentration, the blood glucose information is read by using the apparatus for non-invasive glucose monitoring of the disclosure to detect the glucose information (e.g., concentration of glucose) in the eyeball (e.g., aqueous humor within the eyeball). Since the light intensity difference (e.g., absorption energy intensity difference and optical angular intensity difference) caused by the environmental impact may be avoided by comparing the characteristic intensity and the reference intensity provided by the reference component 128, the internal calibration may be performed to obtain a more precise glucose information, thereby enhancing an accuracy of the blood glucose information (e.g., concentration of blood glucose) and may also calibrating the opto-element system. In addition, when establishing personal parameters for user with individual differences, through relationship with the reference component 128, the glucose may be analyzed using data collected during the first lancing, thus no additional lancing is required later.

The apparatus for non-invasive glucose monitoring 100 may further selectively comprise a beam splitter 130. The beam splitter 130 transmits the light 110 from the beam splitter 104 to the reference component 128 and the light information analysis unit 116, respectively. In the present exemplary embodiment, the light 110 reflected by the reference component 128 is transmitted to the beam splitter 104 through the beam splitter 130 and then transmitted to the set of photo detectors 106 through the beam splitter 104, but the disclosure is not limited thereto. One of ordinary skill in the art would be able to adjust relative positions between the reference component 128 and the beam splitter 130 according to actual requirements. Moreover, in the present exemplary embodiment, even though the reference component 128 and the light information analysis unit 116 are positioned at different sides of the beam splitter 130, but the disclosure is not limited thereto. In another embodiment, the reference component 128 and the light information analysis unit 116 may also be positioned at the same side of the beam splitter 130. In addition, the positions of the reference component 128 and the light information analysis unit 116 in FIG. 1A may also be interchanged.

The apparatus for non-invasive glucose monitoring 100 may further selectively comprise at least one of a shutter 132 and a shutter 134. The shutter 132 is disposed on the first optical path between the beam splitter 104 and the eyeball 200. The shutter 134 is disposed on the second optical path between the beam splitter 104 and the reference component 128. Before performing the measurement to the eyeball 200, the shutter 132 may firstly be closed. Until the light information analysis unit 116 makes sure that the energy generated by the light 110 emitted from the light source 102 is unable to cause any harm to the eyeball 200, then the shutter 132 is opened. In addition, before the set of photo detectors 106 obtains the reference intensity of the light 110 reflected by the reference component 128 from the second optical path, the shutter 134 may firstly be opened. Until the set of photo detectors 106 obtains the reference intensity, then the shutter 134 is closed.

According to the above descriptions, the light intensity difference (e.g., absorption energy intensity difference and optical angular intensity difference) caused by the environmental impact may be avoided with the reference component 128, and thus the apparatus for non-invasive glucose monitoring 100 may perform the internal calibration so as to obtain a more precise glucose information, thereby enhancing the accuracy of the blood glucose information (e.g., concentration of blood glucose).

The apparatus for non-invasive glucose monitoring 100 may further selective comprise an eye positioning device 136. The eye positioning device 136 comprises a beam splitter 138 and a camera 140.

The beam splitter 138 is disposed on the first optical path between the beam splitter 104 and the eyeball 200. The beam splitter 138, for example, is a beam splitter controlling a proportion of transmission and reflection according to the wavelength.

The camera 140 receives an image information transmitted by the beam splitter 138. The camera 140 may be coupled to the processing unit 108. The camera 140, for example, is a microcamera. When the camera 140 may receive the light 110 emitted from the light source 102, the image information may be a position on the eyeball 200 irradiated by the light 110. The image information may help to determine that whether the light 110 falls within an accurate measuring position of the eyeball (e.g., pupil). Moreover, the camera 140 may also be used in performing user identity matching, such that the camera 140 may be used to identify the iris of the eye, and thus, in addition to enhancing personal information security, it would be more convenient for the data processing on remote medical care and telemedicine care.

The eye positioning device 136 may further selectively comprise a light source 142. The light source 142 emits a light 144, the light 144 is leaded into the eyeball 200 by the beam splitter 138, and the light 144 reflected by the eyeball 200 is then transmitted to the camera 140 through the beam splitter 138. The light source 142, for example, is a visible light source or an invisible light source. When the light source 142 is the visible light source, the light source 142 may also be used as a simple eye-alignment positioning device for aligning a sight 150 of the eye to the eye-alignment positioning device to perform an alignment, thereby determining a measuring position of the eyeball. The light source 142, for example, is a light-emitting diode, a laser diode or an organic light-emitting diode. In another embodiment, when the light source 142 is the invisible light source, the apparatus for non-invasive glucose monitoring 100 may further selectively comprise other eye-alignment positioning device, such as signs, embossed patterns or so forth.

The eye positioning device 136 may further selectively comprise a beam splitter 146. The light 144 emitted from the light source 142 is transmitted to the beam splitter 138 through the beam splitter 146, but the disclosure is not limited thereto. One of ordinary skill in the art would be able to choose the means for transmitting the light 144 emitted from the light source 142 to the beam splitter 138 according to the actual requirements, as long as the light 144 emitted from the light source 142 is able to be transmitted to the beam splitter 138.

When the camera 140 may receive the light 144 emitted from the light source 142, the image information may be a position on the eyeball 200 irradiated by the light 144. Now, the light 110 and the light 144 transmitted to the eyeball 200 through the beam splitter 138 have a corresponding optical path relationship therebetween, and this corresponding optical path relationship, for example, are coaxial or non-coaxial. With the image information of the position on the eyeball 200 irradiated by the light 144 and the corresponding optical path relationship, the position on the eyeball 200 irradiated by the light 110 may be obtained, and thus it is able to determine that whether the light 110 falls on the accurate measuring position of the eyeball (e.g., pupil). The image information, for example, is a pattern formed with light spots.

For instance, when the light 110 and the light 144 transmitted to the eyeball 200 through the beam splitter 138 are coaxial, the position on the eyeball 200 irradiated by the light 144 is then equivalent to the position on the eyeball 200 irradiated by the light 110, so that the light 144 received by the camera 140 may acquire the position on the eyeball 200 irradiated by the light 110, and thus it is able to determine whether the light 110 falls on the accurate measuring position of the eyeball (e.g., pupil).

Moreover, when the light 110 and the light 144 transmitted to the eyeball 200 through the beam splitter 138 are non-coaxial, with the known corresponding relationship (e.g., included angle) between the optical paths of the light 110 and the light 144 transmitted to the eyeball 200 through the beam splitter 138, the position on the eyeball 200 irradiated by the light 110 may be calculated from the light 144 received by the camera 140, and thus it is able to determine whether the light 110 falls on the accurate measuring position of the eyeball (e.g., pupil).

In the present exemplary embodiment, the light 110 and the light 144 transmitted to the eyeball 200 through the beam splitter 138 are taken as coaxial for the purpose of illustration, but the disclosure is not limited thereto. One of ordinary skill in the art, based on the contents of the disclosure, would be able to set the light 110 and the light 144 transmitted to the eyeball 200 through the beam splitter 138 as non-coaxial for performing the measurement.

When the light 110 is determined as falling on the accurate measuring position of the eyeball, the monitoring of the glucose may be performed. In addition, when the light 110 is determined as not falling on the accurate measuring position of the eyeball, an active alignment adjustment method or a passive alignment adjustment method may be adopted.

The active alignment adjustment method may perform the alignment of the eyeball 200 by adjusting relative positions between the eyeball 200 and the light 110. For instance, the user may be asked to adjust the position of the eyeball 200, or a beam focusing position of the light 110 may be adjusted. In addition, the eye positioning device 136 may further selectively comprise a lens system 148. The lens system 148 is disposed on the first optical path between the light source 102 and the beam splitter 104, and is configured to dynamically adjust the beam focusing position of the light 110 in order to align the measuring position of the eyeball, so that a measuring signal can be accurately and stably outputted. In addition, as the lens system 148 may enable the focus to motion scan on an optical axis, scans in correspondence to different depths of an analyte (e.g., human eye) may be performed, thereby capable of actively measuring values of other areas. Moreover, when the light 110 is determined as not falling on the accurate measuring position of the eyeball, it may also set to not measure, not record or not adopt any information regarding the non-accurate measuring position of the eyeball, and only until the light 110 falls on the accurate measuring position of the eyeball, the monitoring of the glucose is to be performed.

The passive alignment adjustment method may obtain the accurate glucose information through a backend arithmetic processing of a deviation value between the position of the light 110 falling on the eyeball 200 and the accurate measuring position of the eyeball.

In the present exemplary embodiment, the light source 142 is taken as the visible light source for the purpose of illustration, so that the sight of the eye is enabled to align to the light source 142 for performing the alignment and the measurement, but the disclosure is not limited thereto. In another embodiment, no matter the light source 142 is the visible light source or the invisible light source, the alignment and the measurement may also be performed while under the condition that the sight of the eye is not aligned to the light source 142.

According to the above descriptions, measurement error due to the light 110 not being fell on the accurate measuring position of the eyeball may be avoided with the eye positioning device 136, and thus the apparatus for non-invasive glucose monitoring 100 may obtain a more precise glucose information, thereby enhancing the accuracy of the blood glucose information (e.g., concentration of blood glucose).

The apparatus for non-invasive glucose monitoring 100 may further selectively comprise a joint element 124. An end of the element 124 is connected to a light outlet of the apparatus for non-invasive glucose monitoring 100, and another end of the joint element 124 is used for relying on an outer corner an eye. Moreover, the apparatus for non-invasive glucose monitoring 100 may further selectively comprise a protective cover 126 disposed on a surface of the joint element 124 that is used for relying on the outer corner of eye. The protective cover 126 is, for example, a disposable protective cover.

According to the first exemplary embodiment, the apparatus for non-invasive glucose monitoring 100 may simultaneously analyze the optical angular difference and the absorption energy difference between the light 110 emitted from the light source 102 and the light 110 transmitted to the set of photo detectors 106, thus obtaining the glucose information (e.g., concentration of glucose), and since the glucose concentration in the eyeball 200 (e.g., aqueous humor within eyeball) has a corresponding relationship with a blood glucose concentration, the blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball).

Moreover, the apparatus for non-invasive glucose monitoring 100 may be miniaturized in applications, for example, used in form of a headband or used in collaboration with glasses, so as to improve utilization convenience. In addition, the utilization environment of the apparatus for non-invasive glucose monitoring 100 has no special restriction, and thus may be utilized indoors or outdoors.

Figure 2:
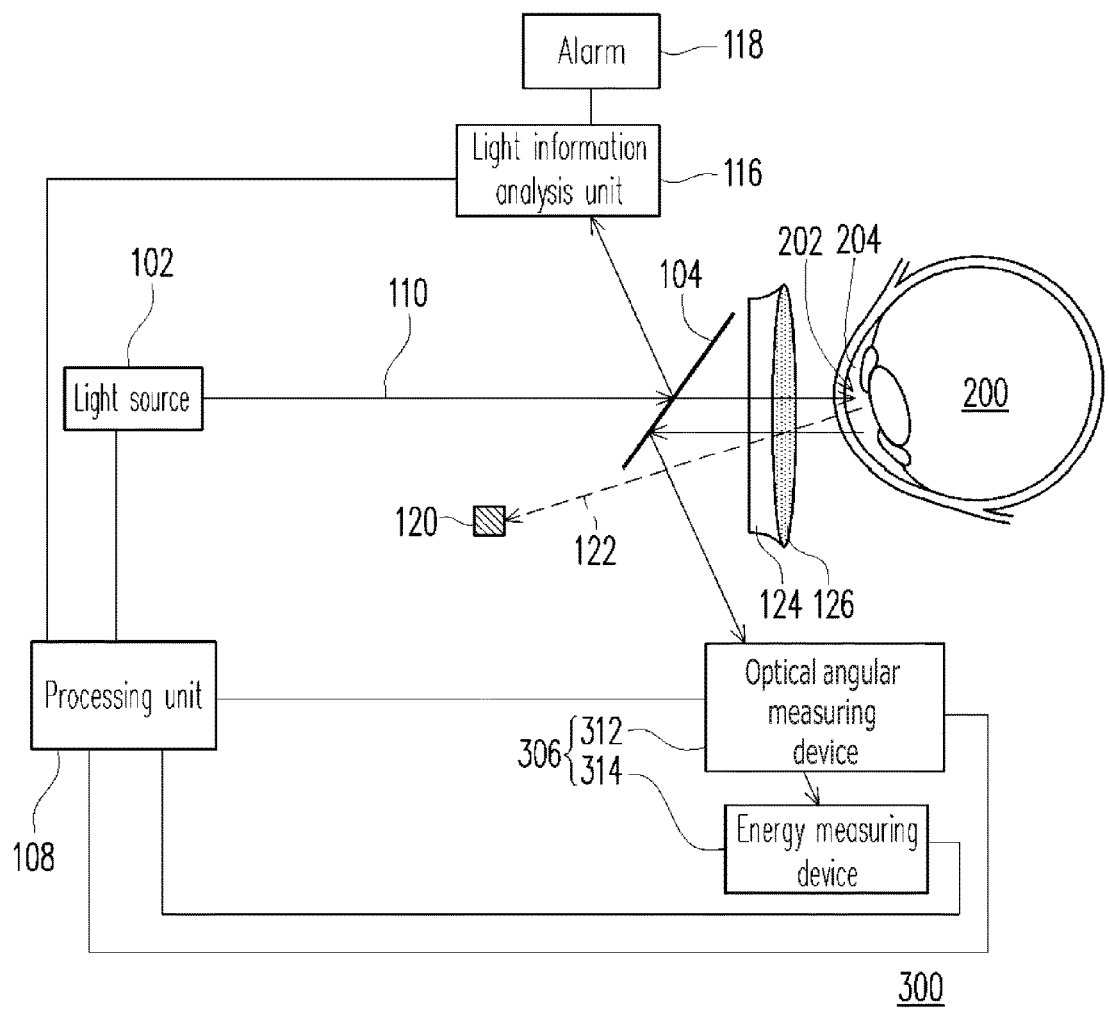
FIG. 2 is a schematic diagram illustrating an apparatus for non-invasive glucose monitoring in accordance with a second exemplary embodiment.

FIG. 2 is a schematic diagram illustrating an apparatus for non-invasive glucose monitoring in accordance with a second exemplary embodiment.

Referring to FIG. 1A and FIG. 2, a difference between the apparatus for non-invasive glucose monitoring 300 of the second exemplary embodiment and the apparatus for non-invasive glucose monitoring 100 of the first exemplary embodiment is that an optical angular measuring device 312 and an energy measuring device 314 in a set of photo detectors 306 of the second exemplary embodiment are located at a same side of the beam splitter 104, and the optical angular measuring device 112 and the energy measuring device 114 in the set of photo detectors 106 of the first exemplary embodiment are located at two sides of the beam splitter 104, respectively. The optical angular measuring device 312 and the energy measuring device 314 are, for example, coupled to the processing unit 108, respectively, but the disclosure is not limited thereto. Compositions, coupling relations and functions of the other components of the apparatus for non-invasive glucose monitoring 300 of the second exemplary embodiment are similar to that of the apparatus for non-invasive glucose monitoring 100 of the first exemplary embodiment, so that detailed descriptions thereof are not repeated.

In the present exemplary embodiment, the set of photo detectors 306 is, for example, used to measure the light 110 reflected from the eyeball 200 and then reflected by the beam splitter 104. The light 110 to be measured is first transmitted to the optical angular measuring device 312 for measuring the optical angular information, and then transmitted to the energy measuring device 314 for measuring the absorption energy information. In another exemplary embodiment, the set of photo detectors 306 may also be used to measure the light 110 reflected from the eyeball 200 and then passed through the beam splitter 104.

In another exemplary embodiment, the apparatus for non-invasive glucose monitoring 300 further comprises another set of the optical angular measuring device 312 and the energy measuring device 314, so that the apparatus for non-invasive glucose monitoring 300 simultaneously has two sets of the optical angular measuring device 312 and the energy measuring device 314 for respectively measuring the optical angular information and the absorption energy information of the light 110 reflected from the eyeball 200 and then passed through the beam splitter 104, and for measuring the optical angular information and the absorption energy information of the light 110 reflected from the eyeball 200 and then reflected by the beam splitter 104.

Similarly, the apparatus for non-invasive glucose monitoring 300 of the second exemplary embodiment may simultaneously analyze the optical angular difference and the absorption energy difference between the light 110 emitted from the light source 102 and the light 110 transmitted to the set of photo detectors 306 to obtain the glucose information (e.g., concentration of glucose), and since the concentration of glucose in the eyeball 200 (e.g., aqueous humor within eyeball) has a relationship with a blood glucose concentration, the blood glucose information (e.g., concentration of blood glucose) with a high accuracy is read, through this corresponding relationship, by using the apparatus for non-invasive glucose monitoring of the disclosure to detect the glucose information (e.g., concentration of glucose) in the eyeball (e.g., aqueous humor within the eyeball). Moreover, the apparatus for non-invasive glucose monitoring 300 may be miniaturized, so that it is convenient in utilization, and may be utilized indoors or outdoors.

Figure 3:
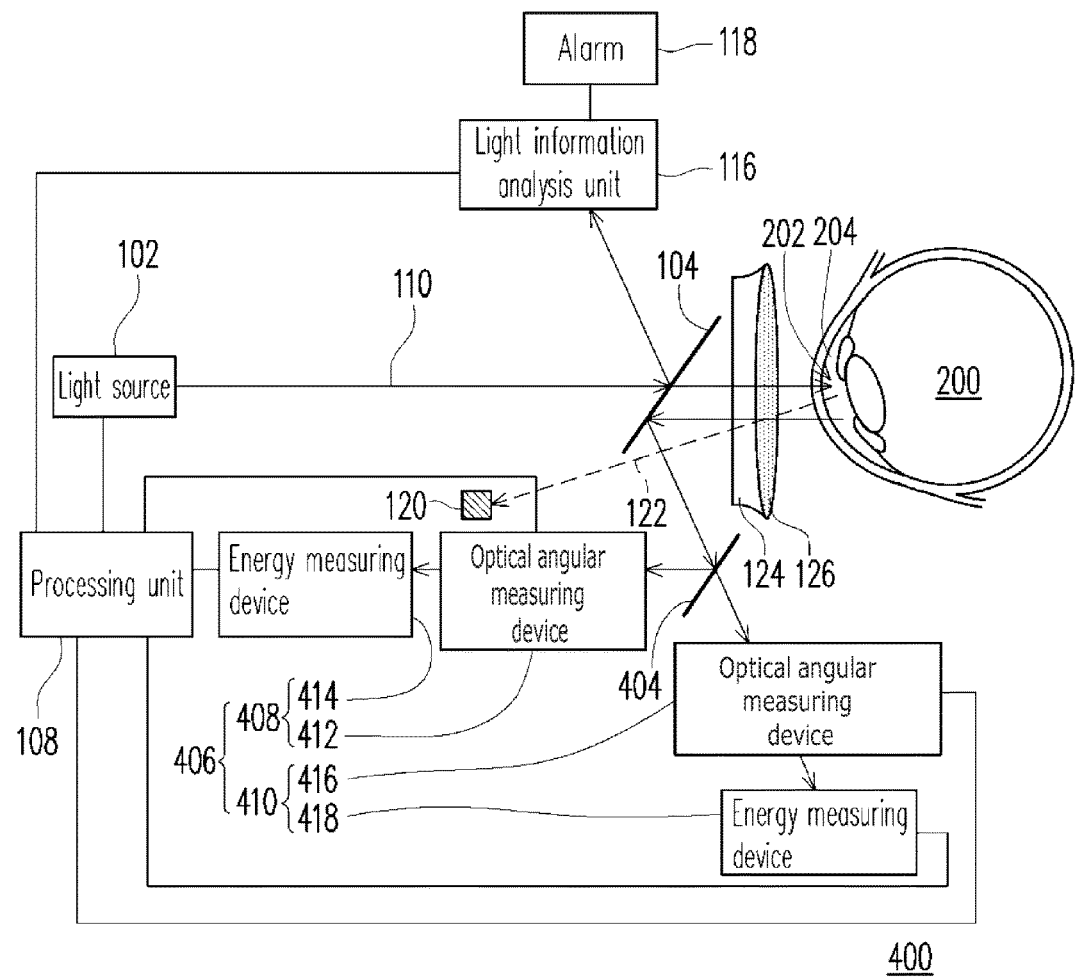
FIG. 3 is a schematic diagram illustrating an apparatus for non-invasive glucose monitoring in accordance with a third exemplary embodiment.

FIG. 3 is a schematic diagram illustrating an apparatus for non-invasive glucose monitoring in accordance with a third exemplary embodiment.

Referring to FIG. 1A and FIG. 3, a difference between an apparatus for non-invasive glucose monitoring 400 of the third exemplary embodiment and the apparatus for non-invasive glucose monitoring 100 of the first exemplary embodiment is that the apparatus for non-invasive glucose monitoring 400 of the third exemplary embodiment further comprises a beam splitter 404, and a set of photo detectors 406 comprises a first photo detector 408 and a second photo detector 410. Compositions, coupling relations and functions of the other components of the apparatus for non-invasive glucose monitoring 400 of the third exemplary embodiment are similar to that of the apparatus for non-invasive glucose monitoring 100 of the first exemplary embodiment, so that detailed descriptions thereof are not repeated.

The beam splitter 404 transmits the light 110 reflected from the eyeball 200 and then transmitted through the beam splitter 104 to the set of photo detectors 406. The beam splitter 404 is, for example, an optical film, an optical lens, an optical grating, a diffractive optical element or a combination of any the above elements.

The first photo detector 408 is used to measure the light 110 reflected by the beam splitter 404, and the second photo detector 410 is used to measure the light 110 passed through the beam splitter 404. The first photo detector 408 comprises an optical angular measuring device 412 and an energy measuring device 414, and the second photo detector 410 comprises an optical angular measuring device 416 and an energy measuring device 418. The light 110 to be measured is, for example, first transmitted to the optical angular measuring device 412 (or 416) for measuring the optical angular information, and then transmitted to the energy measuring device 414 (418) for measuring the absorption energy. Wherein, compositions of the optical angular measuring devices 412, 416 are similar to that of the optical angular measuring device 112, and compositions of the energy measuring devices 414, 418 are similar to the energy measuring device 114, so that descriptions thereof are not repeated. When the first photo detector 408 and the second photo detector 410 in the apparatus for non-invasive glucose monitoring 400 may simultaneously measure the optical angular information and the absorption energy, by cross-comparing the obtained two sets of the optical angular information and the absorption energy, the optical angular difference and the absorption energy difference between the light 110 emitted from the light source 102 and the light 110 transmitted to the set of photo detectors 406 may be analyzed to obtain the glucose information (e.g., concentration of glucose), and since the glucose concentration in the eyeball 200 (e.g., aqueous humor within eyeball) has a relationship with the concentration of blood glucose, the blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball). The optical angular measuring devices 412, 416 and the energy measuring devices 414, 418 are, for example, respectively coupled to the processing unit 108, but the disclosure is not limited thereto.

It is noted that when the optical angular measuring devices 412, 416 are all passive optical angular measuring devices and respectively comprise a polarizer, the polarizers in the optical angular measuring devices 412, 416 are, for example, one of a horizontal polarizer and a vertical polarizer, or two sets of polarizers with known optical angular angles. If the two sets of the polarizers with known optical angular angles are used, one of the measuring methods thereof is to compare energy differences of the two sets of the polarizers, and according to the energy differences, the optical angular difference within a certain range of glucose concentration is obtained, so as to improve the detection accuracy. Another method is to use the two sets of polarizers with known optical angular angles to determine offset components according to the absorption energy differences, so as to calculate the optical angular information.

In another exemplary embodiment, one of the first photo detector 408 and the second photo detector 410 is, for example, a single optical angular measuring device, and another one of the first photo detector 408 and the second photo detector 410 is, for example, a single energy measuring device.

Although, in the aforementioned exemplary embodiment, the light 110 reflected by the beam splitter 404 and/or the light 110 passed through the beam splitter 404 is one ray of light. However, the light 110 reflected by the beam splitter 404 and/or the light 110 passed through the beam splitter 404 may be divided into two or more rays of light by the beam splitter 404, and then measured by the aforementioned first photo detector 408 and the second photo detector 410.

According to the third exemplary embodiment, the apparatus for non-invasive glucose monitoring 400 may simultaneously analyze the optical angular difference and the absorption energy difference between the light 110 emitted from the light source 102 and the light 110 transmitted to the set of photo detectors 406 to obtain the glucose information (e.g., concentration of glucose), and since the concentration of glucose in the eyeball 200 (e.g., aqueous humor within eyeball) has a relationship with the concentration of blood glucose, the blood glucose information (e.g., concentration of blood glucose) with a high accuracy is read, through this corresponding relationship, by using the apparatus for non-invasive glucose monitoring of the disclosure to detect the glucose information (e.g., concentration of glucose) in the eyeball (e.g., aqueous humor within the eyeball). Moreover, the apparatus for non-invasive glucose monitoring 400 may be miniaturized, so that it is convenient in utilization, and thus may be utilized indoors or outdoors.

Figure 4:
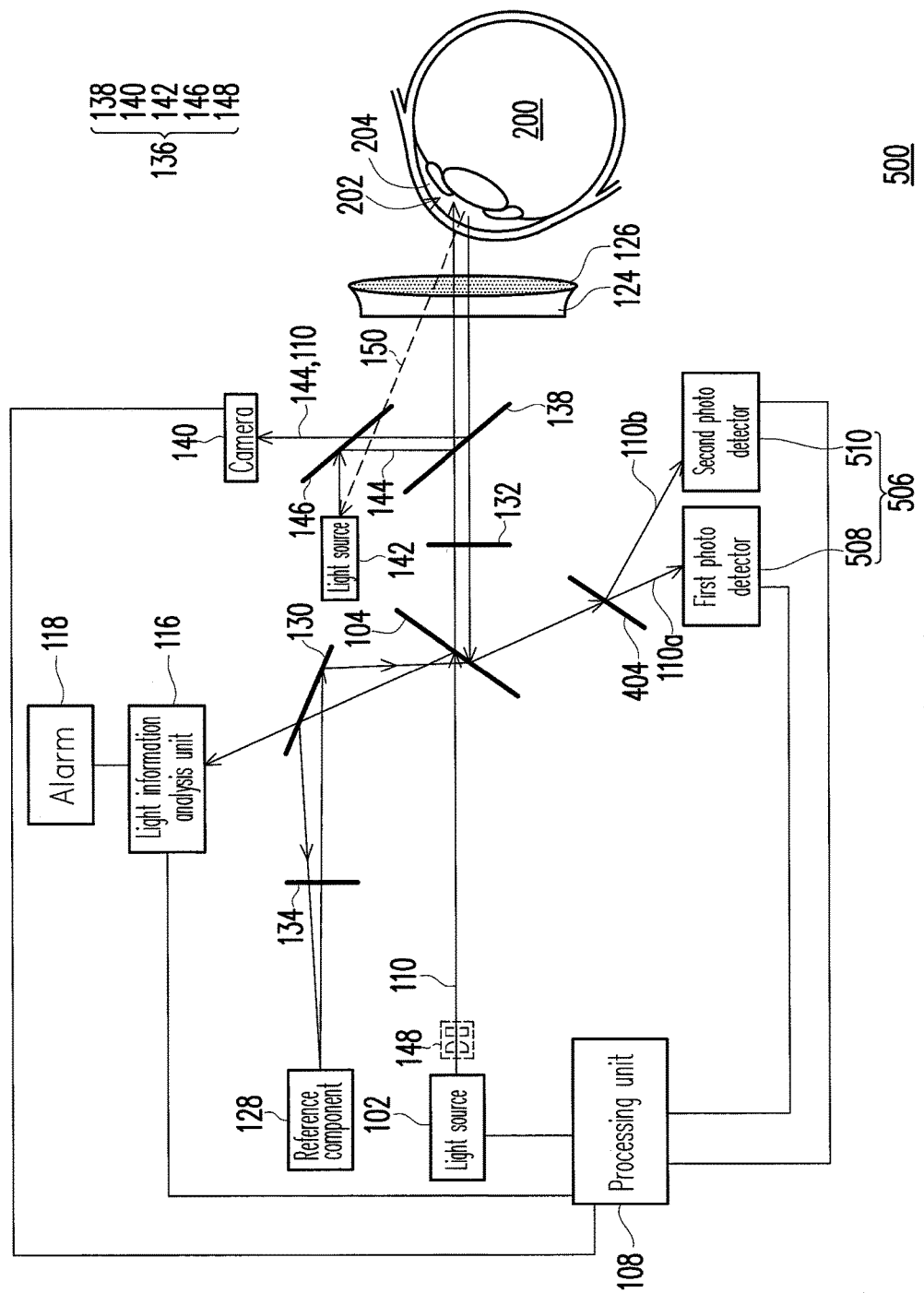
FIG. 4 is a schematic diagram illustrating an apparatus for non-invasive glucose monitoring in accordance with a fourth exemplary embodiment.

FIG. 4 is a schematic diagram illustrating an apparatus for non-invasive glucose monitoring in accordance with a fourth exemplary embodiment.

Referring to FIG. 3 and FIG. 4, a difference between an apparatus for non-invasive glucose monitoring 500 of the fourth exemplary embodiment and the apparatus for non-invasive glucose monitoring 400 of the third exemplary embodiment is that, in the apparatus for non-invasive glucose monitoring 500 of the fourth exemplary embodiment, a set of photo detectors 506 comprises a first photo detector 508 and a second photo detector 510, and the first photo detector 508 and the second photo detector 510 are located at a same side of the beam splitter 404. In the present exemplary embodiment, the first photo detector 508 and the second photo detector 510 are, for example, located at the side of the beam splitter 404 where the light 110 passes there through, and are respectively used to measure two rays of light 110a, 110b generated by the light 110 after passed through the beam splitter 404. One of the first photo detector 508 and the second photo detector 510 is, for example, an optical angular measuring device for measuring the optical angular information, and another one of the first photo detector 508 and the second photo detector 510 is, for example, an energy measuring device for measuring the absorption energy information. The first photo detector 508 and the second photo detector 510 are, for example, coupled to the processing unit 108, respectively, but the disclosure is not limited thereto. Compositions, coupling relations and functions of the other components of the apparatus for non-invasive glucose monitoring 500 of the fourth exemplary embodiment are similar to that of the apparatus for non-invasive glucose monitoring 400 of the third exemplary embodiment, so that detailed descriptions thereof are not repeated.

In another exemplary embodiment, the first photo detector 508 and the second photo detector 510 may also be located at the side of the beam splitter 404, respectively, where the light 110 is reflected, and are used to measure two rays of light generated by reflecting the light 110 through the beam splitter 404.

Although, in the aforementioned exemplary embodiment, the light 110 reflected by the beam splitter 404 and/or the light 110 passed through the beam splitter 404 are the light 110a, 110b, the light 110 reflected by the beam splitter 404 and/or the light 110 passed through the beam splitter 404 may be divided into three or more rays of light by the beam splitter 404 and then measured by the aforementioned first photo detector 508 and the second photo detector 510.

Similarly, the apparatus for non-invasive glucose monitoring 500 of the fourth exemplary embodiment may simultaneously analyze the optical angular difference and the absorption energy difference between the light 110 emitted from the light source 102 and the light 110a,110b transmitted to the photo detector set 506 to obtain the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with a high accuracy is read, through this corresponding relationship, by using the apparatus for non-invasive glucose monitoring of the disclosure to detect the glucose information (e.g., concentration of glucose) in the eyeball (e.g., aqueous humor within the eyeball). Moreover, the apparatus for non-invasive glucose monitoring 500 may be miniaturized, so that it is convenient in utilization, and thus may be utilized indoors or outdoors.

Figure 5:
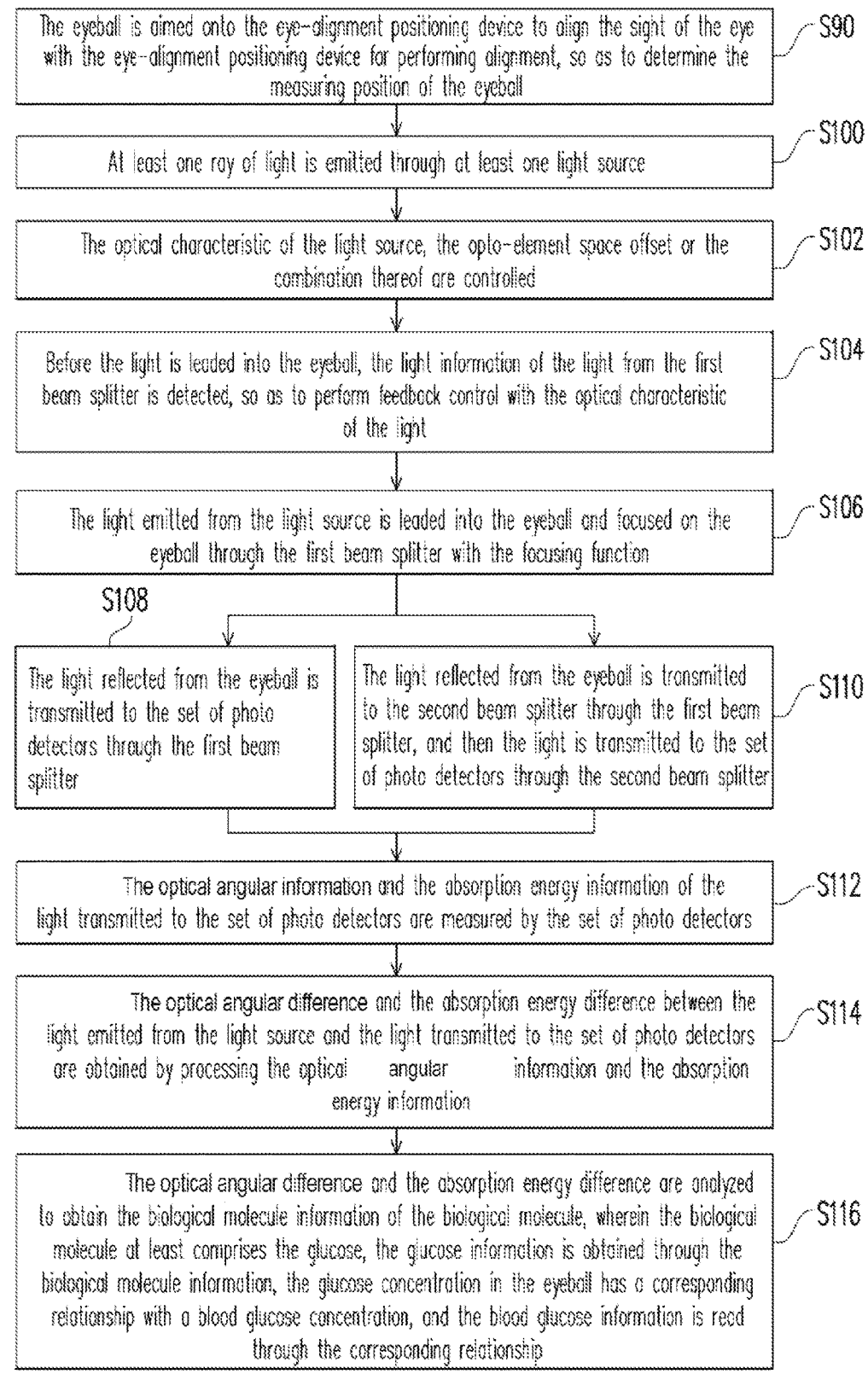
FIG. 5 is a flow chat diagram illustrating a method for a non-invasive glucose monitoring in accordance with a fifth exemplary embodiment.

FIG. 5 is a flow chat diagram illustrating a method for a non-invasive glucose monitoring in accordance with a fifth exemplary embodiment.

With reference to FIG. 5, step S90 may be selected performed for aiming the eyeball onto the eye-alignment positioning device (e.g., light source 142) to align the sight of the eye with the eye-alignment positioning device for performing alignment, wherein the alignment comprises adjusting a relative angle and a position between the optical axis of the eye-alignment positioning device and the sight of the eye, so as to determine a measuring position of the eyeball. Moreover, for the alignment of the eye, in addition to selectively using the eye-alignment positioning device in the step S90, in another embodiment, an eye-alignment method as described in step S108 may also be adopted. In addition, the eye-alignment methods as described in the step S90 and the step S108 may also both be adopted at the same time.

Step S100 is performed to emit at least one ray of light from at least one light source.

Step S102 may be selectively performed for controlling the optical characteristic of the light source, the opto-element offset or the combination thereof, and a change factor is produced thus facilitates in analyzing the glucose information more accurately. Wherein, the light source is used to control an emitting frequency of the light, an intensity of the light, a length of turn-on time of the light, a length of turn-off time of the light, or a combination thereof. The set of photo detectors may assure the light to be measured according to the emitting frequency of the light. Moreover, by controlling the intensity of the light through the light source, it is ensured that the light energy entering the eyeball is unable to cause any harm. In addition, by controlling the length of turn-on time of the light, the length of turn-off time of the light or the combination thereof through the light source, a time required for glucose detection is provided on one hand, and it is ensured that the light energy entering the eyeball is unable to cause any harm on the other hand.

Step S104 may be selectively performed, by which before the light is leaded into the eyeball, the light information of the light from the first beam splitter (e.g., beam splitter 104) is detected, so as to perform a feedback control with the optical characteristic of the light. The light information comprises at least one of the energy information and the position information. The optical characteristic is, for example, a position for emitting energy and/or light.

Step S106 may be selectively performed to avoid the light intensity difference caused by the environmental impact with the reference component. As such, the light intensity difference caused by the environmental impact may be avoided. In addition, execution of the step S104 and the step S106 does not have a specific order.

Step S108 may be selectively performed to align the eye with the eye positioning device (e.g., eye positioning device 136). As such, the measurement error caused due to the light not being fell on the accurate measuring position of the eyeball may be avoided.

Step S110 is performed to enable the light emitted from the light source to be leaded into the eyeball and focused on the eyeball through the first beam splitter (e.g., beam splitter 104) with the focusing function, such that a reflected light reflected from the eyeball is generated.

One of step S112 and step S114 may be performed. Wherein, in step S112, the light reflected from the eyeball is transmitted to the set of photo detectors through the first beam splitter (e.g., beam splitter 104). In step S114, the light reflected from the eyeball is transmitted to the second beam splitter through the first beam splitter (e.g., beam splitter 404), and then the light is transmitted to the set of photo detectors through the second beam splitter (e.g., beam splitter 404).

Step S116 is performed to measure the optical angular information and the absorption energy information of the light transmitted to the set of photo detectors by the set of photo detectors.

Step S118 is performed to obtain the optical angular difference and the absorption energy difference between the light emitted from the light source and the light transmitted to the set of photo detectors by processing the optical angular information and the absorption energy information.

Step S120 is performed to analyze the optical angular difference and the absorption energy difference so as to obtain the information of the biological molecule, wherein the biological molecule at least comprises the glucose, and the glucose information is obtained through the biological molecule information. In addition, since the glucose concentration in the eyeball (e.g., aqueous humor within eyeball) has a corresponding relationship with the concentration of blood glucose, the blood glucose information (e.g., concentration of blood glucose) is read, through this corresponding relationship, by using the apparatus for non-invasive glucose monitoring of the disclosure to detect the glucose information (e.g., concentration of glucose) in the eyeball (e.g., aqueous humor within the eyeball). The biological molecule is, for example, cholesterol, uric acid, water, lactic acid, urea, ascorbic acid, or a combination thereof. Moreover, the biological molecule may comprise an interference molecule therein, and the interference molecule is, for example, different from the measurement target (e.g., glucose), such as cholesterol, uric acid, water, lactic acid, urea, or ascorbic acid. Wherein, ascorbic acid and lactic acid may generate interference to the optical angular information whereas water may generate interference to the absorption energy information. Furthermore, in the step S120, the interference generated by the interference molecule may further be selectively removed. On the other hand, in the step S120, the light intensity difference caused by the environmental impact may further be avoided by selectively comparing the characteristic intensity and the reference intensity provided by the reference component, and thus the internal calibration may be performed for obtaining the more precise glucose information, thereby enhancing the accuracy of the blood glucose information (e.g., concentration of blood glucose).

Variations of the method for non-invasive glucose monitoring and various used devices of the fifth exemplary embodiment have been described in detail in the first to the fourth exemplary embodiments, so that descriptions thereof are not repeated.

According to the above descriptions, in the method for non-invasive glucose monitoring of the fifth exemplary embodiment, since an optical eyeball detecting method is used to measure the glucose information (e.g., concentration of glucose) of the measuring object, the glucose information (e.g., glucose concentration) of the measuring object may be continuously obtained in real time, and since the glucose concentration has a relationship with a blood glucose concentration, the blood glucose information (e.g., concentration of blood glucose) may be read by using the apparatus for non-invasive glucose monitoring of the disclosure to detect the glucose information (e.g., concentration of glucose) in the eyeball (e.g., aqueous humor within the eyeball).

On the other hand, the above-mentioned exemplary embodiment of the apparatus for non-invasive glucose monitoring may further be used in the application of a portable mobile device, so that the portable mobile device has a non-invasive glucose monitoring function. The portable mobile device is, for example, mobile phone, tablet PC, digital camera, and so forth. The following descriptions below are, the exemplary embodiments, for describing a portable mobile device with a non-invasive glucose monitoring function.

Figure 6:
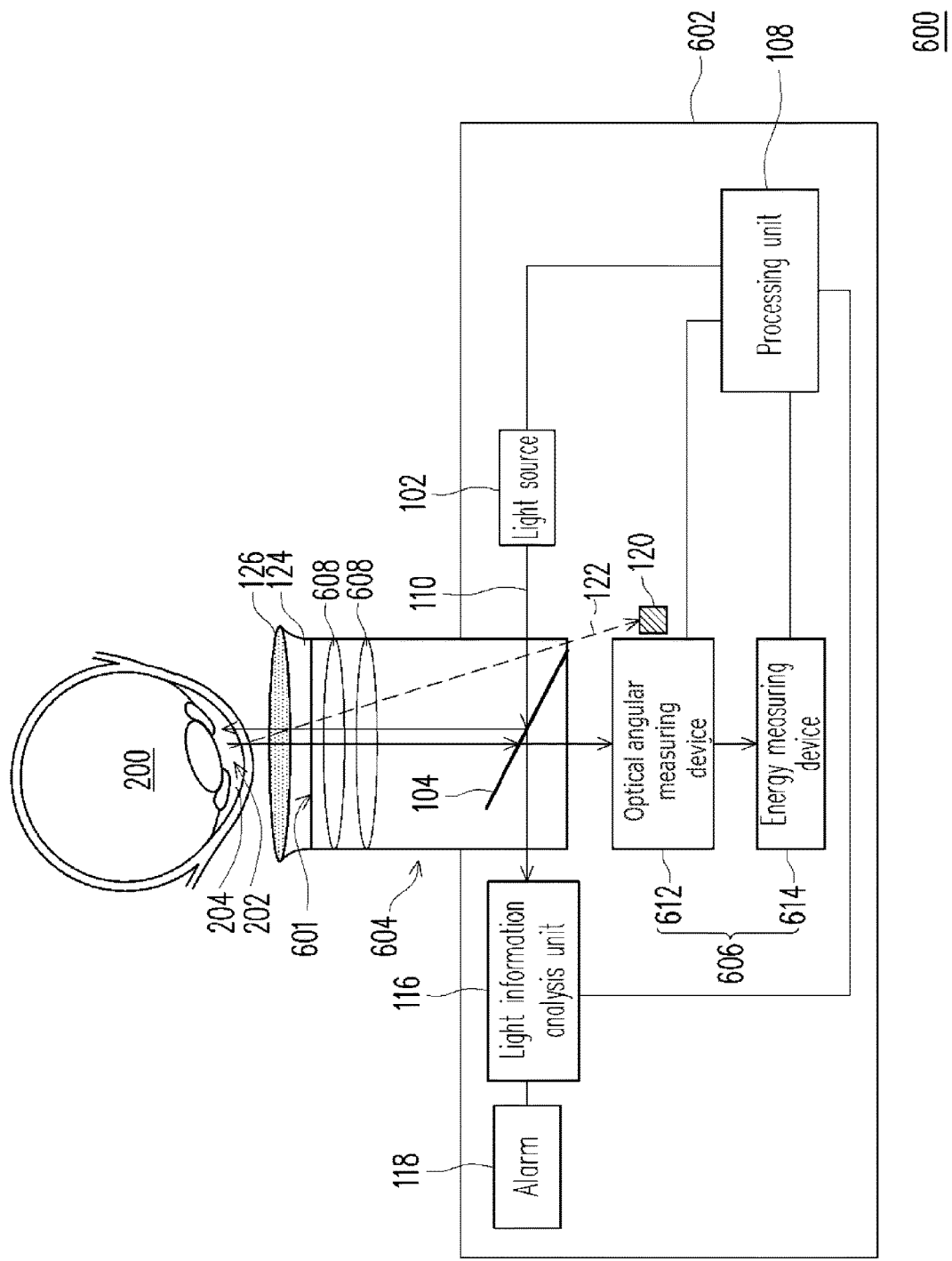
FIG. 6 is a schematic diagram illustrating a portable mobile device with a non-invasive glucose monitoring function in accordance with a sixth exemplary embodiment.

FIG. 6 is a schematic diagram illustrating a portable mobile device with a non-invasive glucose monitoring function in accordance with a sixth exemplary embodiment.

Referring to FIG. 2 and FIG. 6, a difference between a portable mobile device 600 of the sixth exemplary embodiment and the apparatus for non-invasive glucose monitoring 300 of the second exemplary embodiment is that the portable mobile device 600 further comprises a device body 602 and an optical kit 604. The optical kit 604 is disposed on the device body 602, and the optical kit 604 comprises the beam splitter 104 therein. A set of photo detectors 606, the processing unit 108, the light source 102, the light information analysis unit 116, and the alarm 118 are, for example, disposed in the device body 602, but the disclosure is not limited thereto. Moreover, the set of photo detectors 606 comprises an optical angular measuring device 612 and an energy measuring device 614, wherein the portable mobile device 600 uses a light sensing element in a camera module thereof as the energy measuring device 614 in the set of photo detectors 606. The optical angular measuring device 612 and the energy measuring device 614 are, for example, respectively coupled to the processing unit 108, but the disclosure is not limited thereto. The optical angular measuring device 612 is, for example, an active optical angular measuring device or a passive optical angular measuring device. The energy measuring device 614 is, for example, a light sensing element, such as a charge coupled device, a complementary metal oxide semiconductor sensors or a light emitting diode. In addition, the light 110 used by the portable mobile device 600 for glucose monitoring is to be transmitted through a light route of the camera module of the portable mobile device 600. Compositions, coupling relations and functions of the other components of the portable mobile device 600 of the sixth exemplary embodiment are similar to that of the apparatus for non-invasive glucose monitoring 300 of the second exemplary embodiment, and the similar components of the portable mobile device 600 of the sixth exemplary embodiment and of the apparatus for non-invasive glucose monitoring 300 of the second exemplary embodiment are with similar compositions; furthermore, the method for glucose monitoring may be referred to the third exemplary embodiment, so that detailed descriptions thereof are not repeated. In addition, in order to simplify the drawings, the coupling relationship between the camera 140 and the processing unit 108 is not illustrated in FIG. 6 to FIG. 13.

Moreover, in the sixth exemplary embodiment, an end of the joint element 124 is connected to a light outlet 601 of the portable mobile device 600, and another end of the joint element 124 is used for relying on an outer corner of the eye.

On the other hand, the optical kit 604 may further selectively comprise a lens set 608. When the optical kit 604 has the lens set 608, the optical kit 604 may be integrated as a camera lens in camera module of the portable mobile device 600. In addition, whether or not the optical kit 604 has the lens set 608, the camera lens in the camera module of the portable mobile device 600 may be replaced by the optical kit 604 in order to perform the glucose monitoring. In another exemplary embodiment, during the glucose monitoring, the optical kit 604, with the design of the light source, may be externally attached directly on the camera lens of the camera module of the portable mobile device 600.

In the present exemplary embodiment, the light 110 emitted from the light source 102 is leaded into the eyeball 200 and focused on the eyeball 200 through the beam splitter 104. The set of photo detectors 606 is, for example, used to measure the light 110 reflected from the eyeball 200 and then passed through or reflected from the beam splitter 104. The light 110 to be measured is first transmitted to the optical rotatory distribution measuring device 612 for measuring the optical rotatory distribution information, and then transmitted to the energy measuring device 614 for measuring the absorption energy information.

According to the above descriptions, the portable mobile device 600 of the sixth exemplary embodiment may simultaneously analyze the optical angular difference and the absorption energy difference between the light 110 emitted from the light source 102 and the light 110 transmitted to the set of photo detectors 606, thus obtaining a glucose information (e.g., concentration of glucose), and since the concentration of glucose in the eyeball 200 (e.g., aqueous humor within eyeball) has a corresponding relationship with the concentration of blood glucose, a blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball). In addition, since the glucose monitoring function is integrated to the portable mobile device 600, it is convenient in utilization. Moreover, telemedicine care may be provided by using the program or network of the portable mobile device 600 to connect to the cloud.

Figure 7:
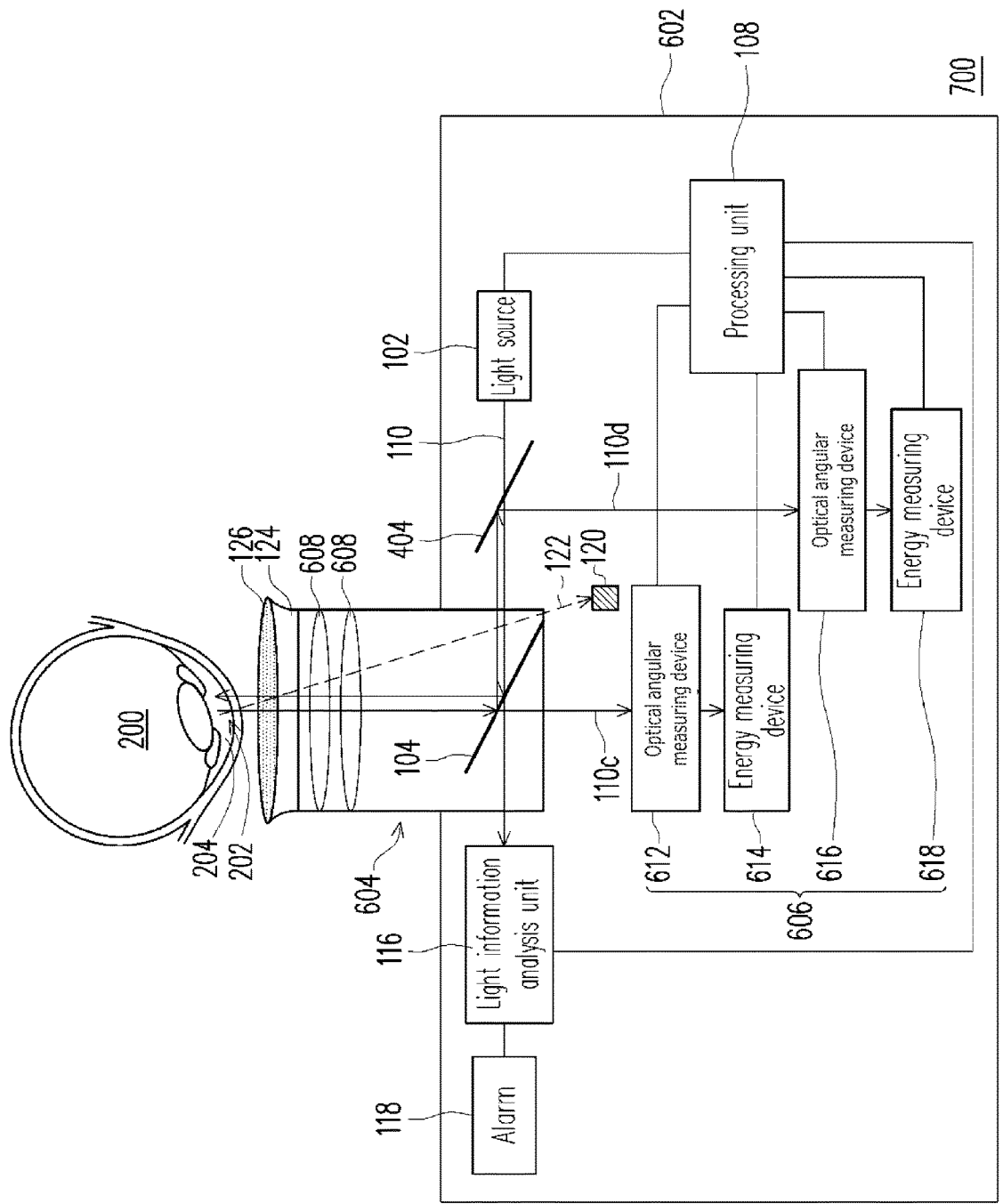
FIG. 7 is a schematic diagram illustrating a portable mobile device with a non-invasive glucose monitoring function in accordance with a seventh exemplary embodiment.

FIG. 7 is a schematic diagram illustrating a portable mobile device with a non-invasive glucose monitoring function in accordance with a seventh exemplary embodiment.

Referring to FIG. 6 and FIG. 7, a difference between a portable mobile device 700 of the seventh exemplary embodiment and the portable mobile device 600 of the sixth exemplary embodiment is that the portable mobile device 700 further comprises the beam splitter 404 (may be referred to the third exemplary embodiment), and the set of photo detectors 606 further comprises an optical angular measuring device 616 and an energy measuring device 618. The optical angular measuring device 616 is, for example, an active optical angular measuring device or a passive optical angular measuring device. The energy measuring device 618 is, for example, a light sensing element, such as a charge coupled device, a complementary metal oxide semiconductor sensors or a light emitting diode. Compositions, coupling relations and functions of the other components of the portable mobile device 700 of the seventh exemplary embodiment are similar to that of the portable mobile device 600 of the sixth exemplary embodiment, and the similar components of the portable mobile device 700 of the seventh exemplary embodiment and of the portable mobile device 600 of the sixth exemplary embodiment are with similar compositions; furthermore, the method for glucose monitoring may be referred to the third exemplary embodiment, so that detailed descriptions thereof are not repeated.

The beam splitter 404 is, for example, to transmit the light 110 reflected from the eyeball 200 and then transmitted through the beam splitter 104 to the set of photo detectors 606. The beam splitter 404 is, for example, an optical film, an optical lens, an optical grating, a diffractive optic element, or a combination of any the above elements.

In the set of photo detectors 606, the optical angular measuring device 612 and the energy measuring device 614 are, for example, used for measuring a ray of light 110 reflected from the eyeball 200 and then passed through the beam splitter 104 reflected from the eyeball 200 and then passed through the beam splitter 104. The light 110c to be measured is, for example, first transmitted to the optical angular measuring device 612 for measuring the optical angular information, and then transmitted to the energy measuring device 614 for measuring the absorption energy. The optical angular measuring device 616 and the energy measuring device 618 are, for example, used for measuring a ray of light 110d reflected from the eyeball 200, transmitted to the beam splitter 404 through the beam splitter 104 to the, and then reflect by the beam splitter 404. The light 110d to be measured is, for example, first transmitted to the optical angular measuring device 616 for measuring the optical angular information, and then transmitted to the energy measuring device 618 for measuring the absorption energy information.

In the present exemplary embodiment, the energy measuring devices 614, 618 are described as two separate components; however, in another exemplary embodiment, the energy measuring devices 614, 618 may be a plurality of different sensing regions on the same light sensing element and may also use the different sensing regions on the light sensing element to sense the light.

Similarly, the portable mobile device 700 of the seventh exemplary embodiment may simultaneously analyze the optical angular difference and the absorption energy difference between the light 110c emitted from the light source 102 and the light 110c, 110d transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball). In addition, since the glucose monitoring function is integrated to the portable mobile device 700, it is convenient in utilization. Moreover, telemedicine care may be provided by using the program or network of the portable mobile device 700 to connect to the cloud.

Figure 8:
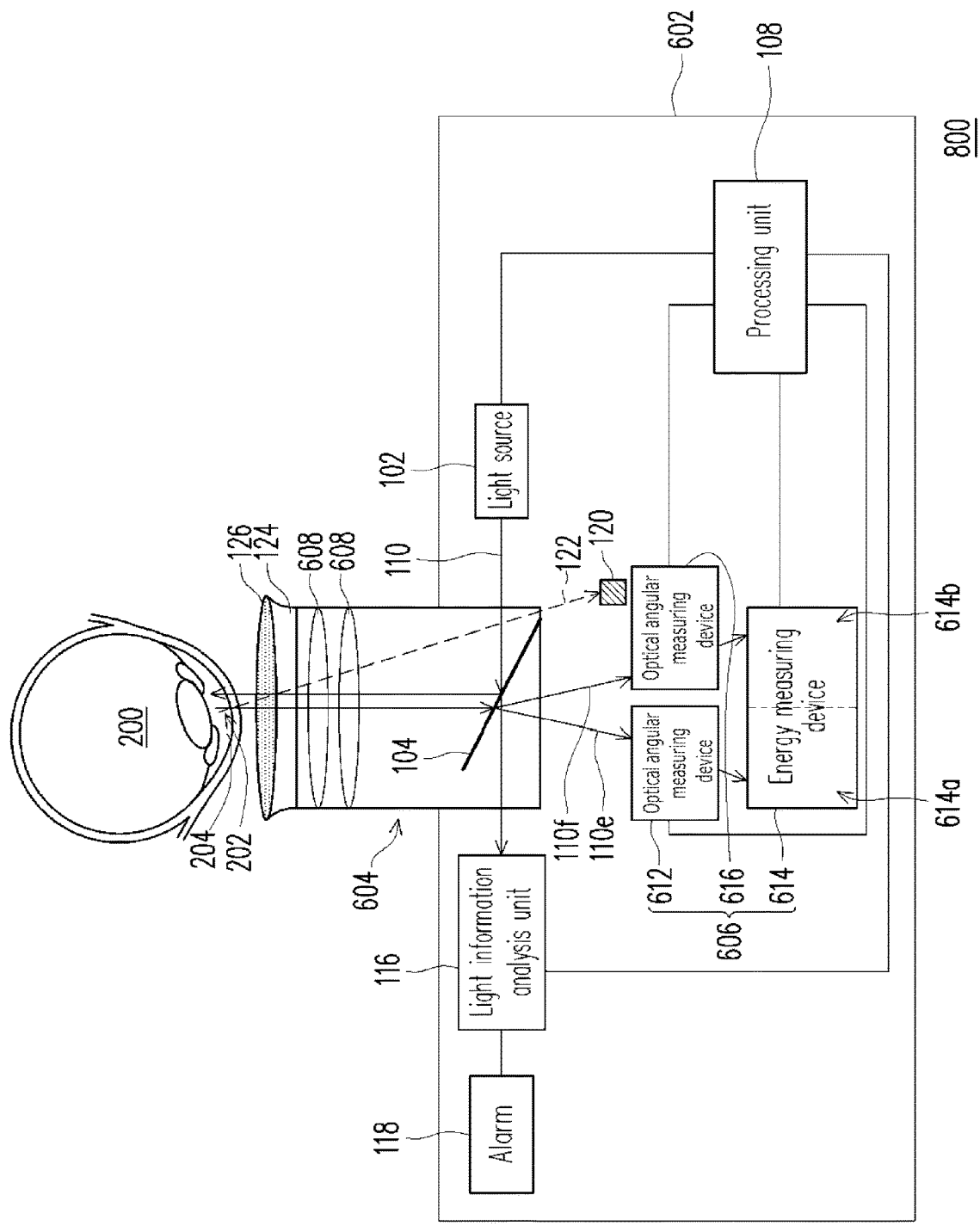
FIG. 8 is a schematic diagram illustrating a portable mobile device with a non-invasive glucose monitoring function in accordance with an eighth exemplary embodiment.

FIG. 8 is a schematic diagram illustrating a portable mobile device with a non-invasive glucose monitoring function in accordance with an eighth exemplary embodiment.

Referring to FIG. 7 and FIG. 8, a difference between a portable mobile device 800 of the eighth exemplary embodiment and the portable mobile device 700 of the seventh exemplary embodiment is that, in the portable mobile device 800, the light 110 may generate two rays of light 110e, 110f after passed through the beam splitter 104, thus not having the beam splitter 404 in the portable mobile device 700. In addition, the set of photo detectors 606 of the portable mobile device 800 has only the energy measuring device 614 not the energy measuring device 618. The energy measuring device 614 comprises a plurality of sensing regions 614a, 614b, wherein the sensing regions 614a, 614b may respectively measure the absorption energy information of the light 110e, 110f. Compositions, coupling relations and functions of the other components of the portable mobile device 800 of the eighth exemplary embodiment are similar to that of the portable mobile device 700 of the seventh exemplary embodiment, and the similar components in the eighth exemplary embodiment and in the seventh exemplary embodiment are with similar compositions; furthermore, the method for glucose monitoring may be referred to the seventh exemplary embodiment, so that detailed descriptions thereof are not repeated.

In the present exemplary embodiment, the same energy measuring device 614 is used to measure the light 110e, 110f. However, in another exemplary embodiment, the portable mobile device 800 may also use two separate energy measuring devices to measure the light 110e, 110f.

It is noted that, in the aforementioned exemplary embodiments, the light 110 being divided into two rays of light 110e, 110f by the beam splitter 104 is taken as an example for the description, but the disclosure is not limited thereto. One of ordinary skill in the art would be able to know that, according to the above exemplary embodiments, when the light 110 is divided into two or more rays of light by the beam splitter 104, the number of the sensing regions on the energy measuring device 614 may also be divided into two or more, so as to respectively correspond to the light from the beam splitter 104, and thus capable of measuring the absorption energy information of the corresponded light, respectively.

Although, in the present exemplary embodiment, the two or more rays of the light received by the energy measuring device 614 is generated by the beam splitter 104, but the disclosure is not limited thereto. In another exemplary embodiment, the two or more rays of the light received by the energy measuring device 614 may also be formed by the light source 102; therefore, the light passed through the beam splitter 104 may be more than two, and now the number of the sensing regions on the energy measuring device 614 may also be divided into more than two, so as to respectively correspond to the light from the beam splitter 104, and thus capable of measuring the absorption energy information of the corresponded light, respectively.

Similarly, the portable mobile device 800 of the eighth exemplary embodiment may simultaneously analyze the optical angular difference and the absorption energy difference between the light 110 emitted from the light source 102 and the light 110e, 110f transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball). In addition, since the glucose monitoring function is integrated to the portable mobile device 800, it is convenient in utilization. Moreover, telemedicine care may be provided by using the program or network of the portable mobile device 800 to connect to the cloud for using the real-time blood glucose data to remind or control medication and to directly inform the medical unit to perform first aid in case of emergency situation.

Figure 9:
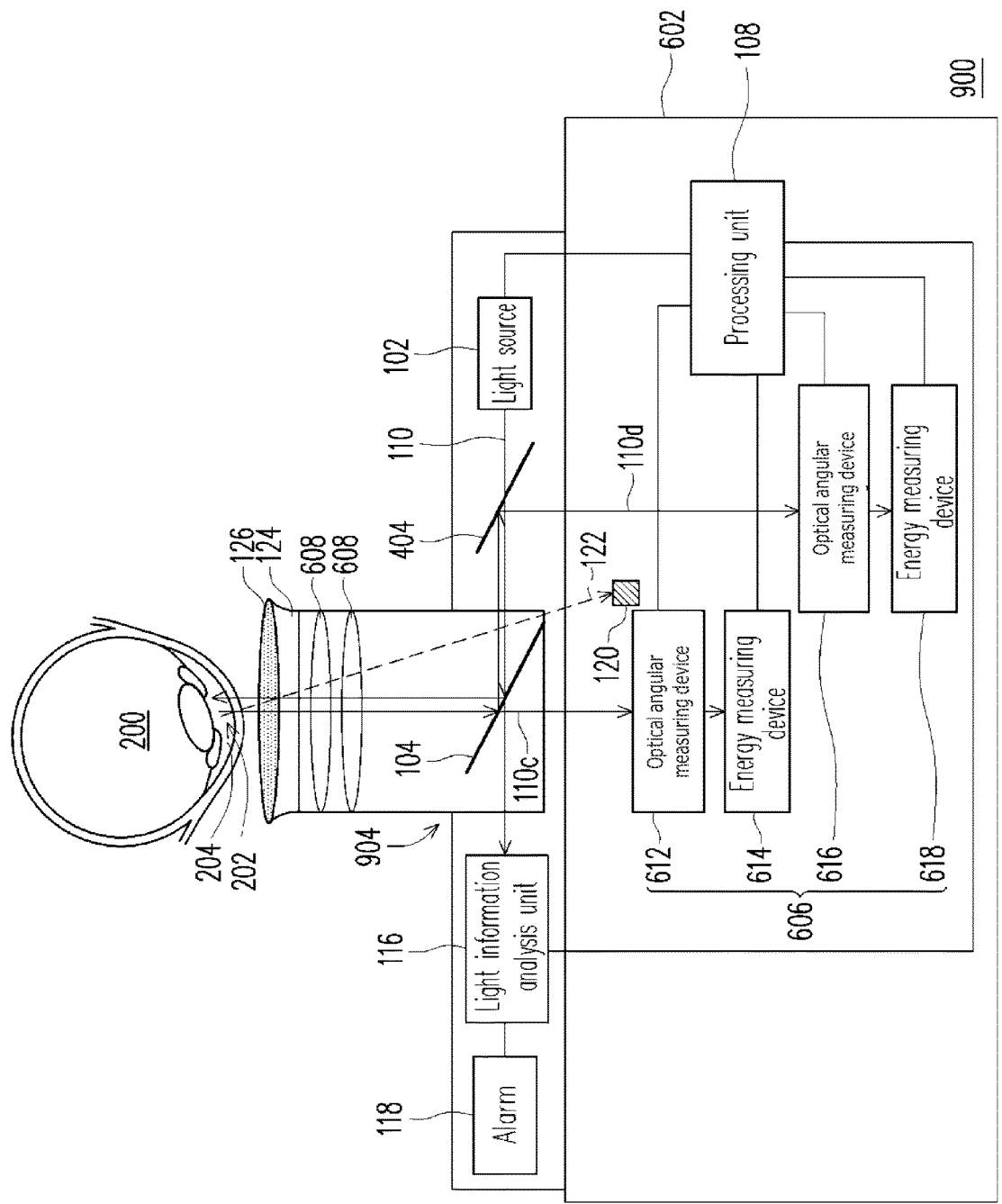
FIG. 9 is a schematic diagram illustrating a portable mobile device with a non-invasive glucose monitoring function in accordance with a ninth exemplary embodiment.

FIG. 9 is a schematic diagram illustrating a portable mobile device with a non-invasive glucose monitoring function in accordance with a ninth exemplary embodiment.

Referring to FIG. 7 and FIG. 9, a difference between a portable mobile device 900 of the ninth exemplary embodiment and the portable mobile device 700 of the seventh exemplary embodiment is that the composition of an optical kit 904 of the ninth exemplary embodiment is different from the composition of the optical kit 604 of the seventh exemplary embodiment. The optical kit 904 is externally attached and disposed on the device body 602, and the optical kit 904 other than comprises the beam splitter 104 and the lens set 608, also comprises the light source 102 and the beam splitter 404. In addition, the optical kit 904 may further selectively comprise the light information analysis unit 116 and the alarm 118. Compositions, coupling relations and functions of the other components of the portable mobile device 900 of the ninth exemplary embodiment are similar to that of the portable mobile device 700 of the seventh exemplary embodiment, and the similar components in the ninth exemplary embodiment and in the seventh exemplary embodiment are with similar compositions; furthermore, the method for glucose monitoring may be referred to the seventh exemplary embodiment, so that detailed descriptions thereof are not repeated.

Similarly, the portable mobile device 900 of the ninth exemplary embodiment may simultaneously analyze the optical angular difference and the absorption energy difference between the light 110 emitted from the light source 102 and the light 110c, 110d transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball). In addition, since the glucose monitoring function is integrated to the portable mobile device 900, it is convenient in utilization. Moreover, telemedicine care may be provided by using the program or network of the portable mobile device 900 to connect to the cloud.

It is noted that the concept of the externally connected optical kit 904 of the portable mobile device 900 in the ninth exemplary embodiment may also be applied to the sixth to the eighth exemplary embodiment.

Figure 10:
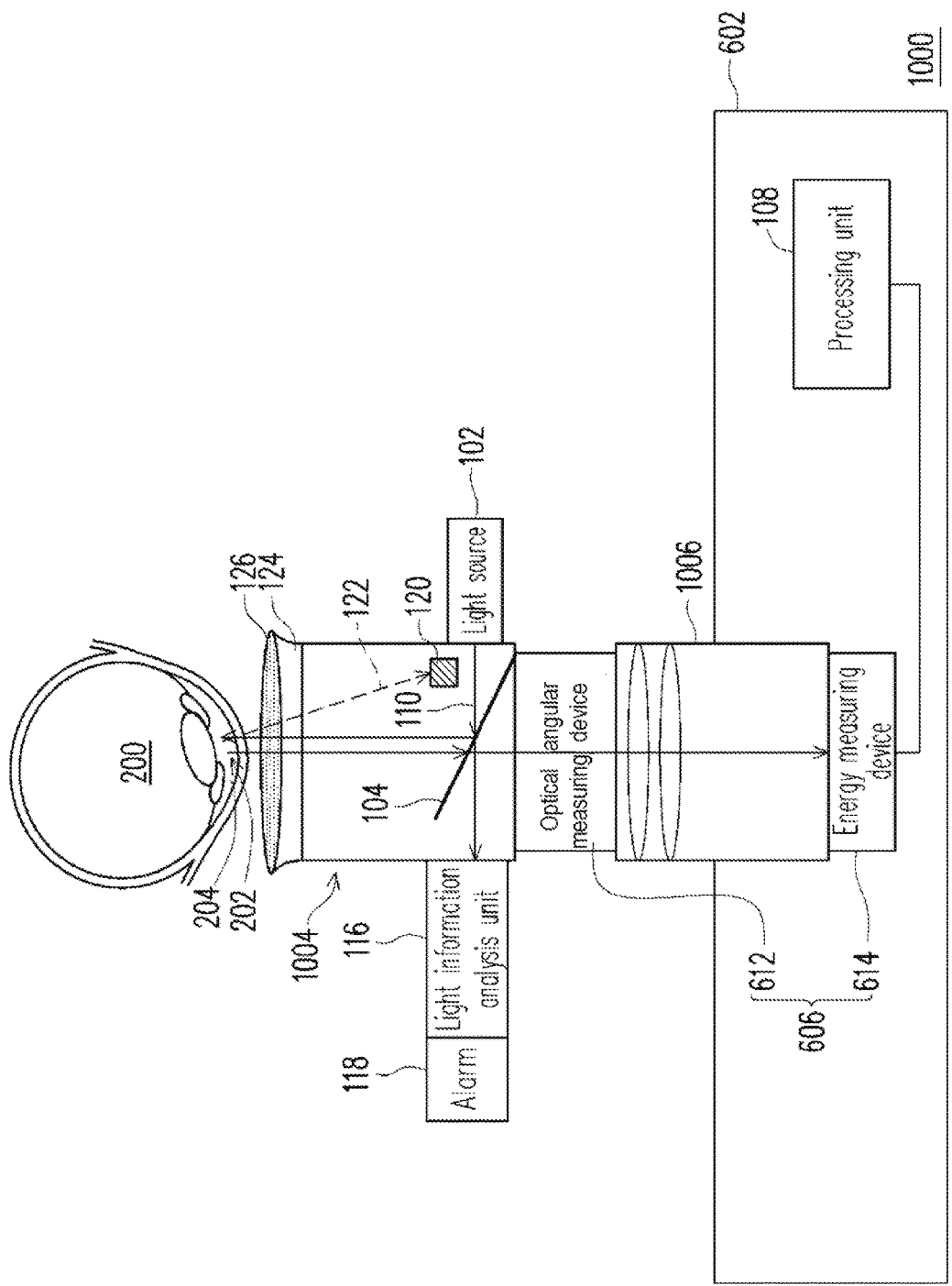
FIG. 10 is a schematic diagram illustrating a portable mobile device with a non-invasive glucose monitoring function in accordance with a tenth exemplary embodiment.

FIG. 10 is a schematic diagram illustrating a portable mobile device with a non-invasive glucose monitoring function in accordance with a tenth exemplary embodiment.

Referring to FIG. 6 and FIG. 10, a difference between a portable mobile device 1000 of the tenth exemplary embodiment and the portable mobile device 600 of the sixth exemplary embodiment is that the composition of an optical kit 1004 of the tenth exemplary embodiment is different from the composition of the optical kit 604 of the sixth exemplary embodiment. The optical kit 1004 is externally attached and disposed on a lens 1006 of the portable mobile device 1000, and the optical kit 1004 comprises the beam splitter 104, the light source 102 and the optical angular measuring device 612. In addition, the optical kit 1004 may further selectively comprise the light information analysis unit 116 and the alarm 118. One of ordinary skill in the art would be able to couple the light source 102, the optical angular measuring device 612 and the light information analysis unit 116 with the processing unit 108 using the most suitable method, so that detailed descriptions are not repeated. Compositions, coupling relations and functions of the other components of the portable mobile device 1000 of the tenth exemplary embodiment are similar to that of the portable mobile device 600 of the sixth exemplary embodiment, and the similar components in the tenth exemplary embodiment and in the sixth exemplary embodiment are with similar compositions; furthermore, the method for glucose monitoring may be referred to the sixth exemplary embodiment, so that detailed descriptions thereof are not repeated.

When measuring the glucose, the optical angular measuring device 612 and the energy measuring device 614 are, for example, used to measure the light 110 reflected from the eyeball 200 and then passed through the beam splitter 104. The light 110 to be measured is, for example, first transmitted to the optical angular measuring device 612 for measuring the optical angular information, and then transmitted to the energy measuring device 614, after passed through the lens 1006, for measuring the absorption energy information.

Similarly, the portable mobile device 1000 of the tenth exemplary embodiment may simultaneously analyze the optical angular difference and the absorption energy difference between the light 110 emitted from the light source 102 and the light 110 transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball). In addition, since the glucose monitoring function is integrated to the portable mobile device 1000, it is convenient in utilization. Moreover, telemedicine care may be provided by using the program or network of the portable mobile device 1000 to connect to the cloud.

Figure 11:
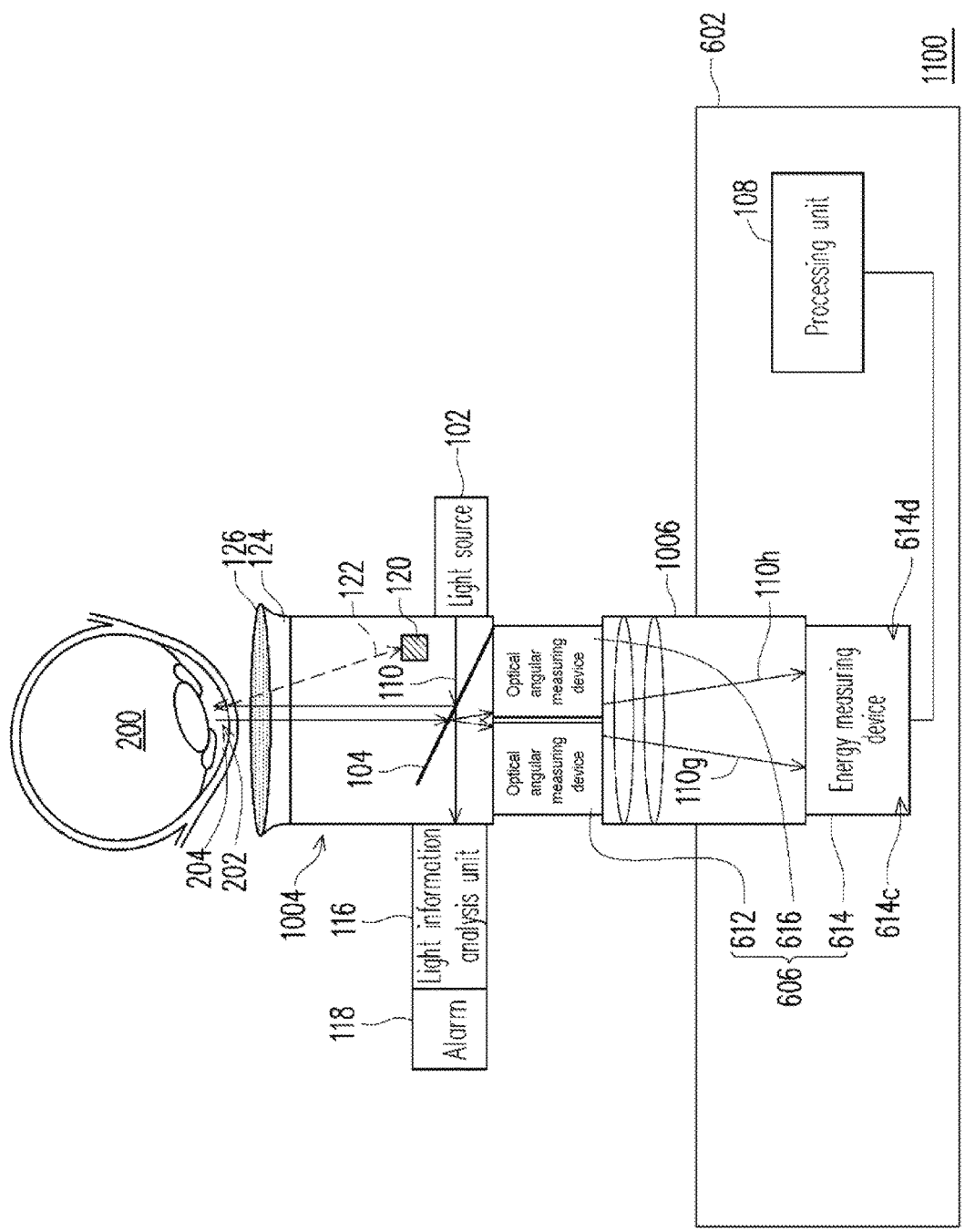
FIG. 11 is a schematic diagram illustrating a portable mobile device with a non-invasive glucose monitoring function in accordance with an eleventh exemplary embodiment.

FIG. 11 is a schematic diagram illustrating a portable mobile device with a non-invasive glucose monitoring function in accordance with an eleventh exemplary embodiment.

Referring to FIG. 10 and FIG. 11, a difference between a portable mobile device 1100 of the eleventh exemplary embodiment and the portable mobile device 1000 of the tenth exemplary embodiment is that, in the portable mobile device 1100, the light 110 may generate two rays of light 110*g*, 110*h* after passed through the beam splitter 104. In addition, the set of photo detectors 606 of the portable mobile device 1100 comprises the optical angular measuring devices 612, 616 and the energy measuring device 614. Wherein, the energy measuring device 614 comprises the sensing regions 614*c*, 614*d*. The light 110*g*, 110*h* may measure the optical angular information through the optical angular measuring devices 612, 616, respectively, and then measure the absorption energy information through the sensing regions 614*c*, 614*d* of the energy measuring device 614, respectively. Compositions, coupling relations and functions of the other components of the portable mobile device 1100 of the eleventh exemplary embodiment are similar to that of the portable mobile device 1000 of the tenth exemplary embodiment, and the similar components in the eleventh exemplary embodiment and in the tenth exemplary embodiment are with similar compositions; furthermore, the method for glucose monitoring may be referred to the tenth exemplary embodiment, so that detailed descriptions thereof are not repeated.

In the present exemplary embodiment, the portable mobile device 1100 may measure the light 110*g*, 110*h* by the same energy measuring device 614. However, in another exemplary embodiment, the portable mobile device 1100 may also use two separate energy measuring devices to measure the light 110*g*, 110*h*.

It is noted that, in the aforementioned exemplary embodiments, the light 110 being divided into two rays of light 110*g*, 110*h* by the beam splitter 104 is taken as an example for the description, but the disclosure is not limited thereto. One of ordinary skill in the art would be able to know that, according to the above exemplary embodiments, when the light 110 can be divided into two or more rays of light 110*g*, 110*h* by the beam splitter 104, the number of sensing regions on the energy measuring device 614 may also be divided into two or more, so as to respectively correspond to the light from the beam splitter 104, and thus capable of respectively measuring the absorption energy information of the corresponded light.

Although, in the present exemplary embodiment, the two or more rays of the light received by the energy measuring device 614 is generated by the beam splitter 104, but the disclosure is not limited thereto. In another exemplary embodiment, the two or more rays of the light received by the energy measuring device 614 may also be formed by the light source 102; therefore, the light passed through the beam splitter 104 may be more than two, and now the number of sensing regions on the energy measuring device 614 may also be divided into more than two, so as to respectively correspond to the light from the beam splitter 104, and thus capable of respectively measuring the absorption energy information of the corresponded light.

Similarly, the portable mobile device 1100 of the eleventh exemplary embodiment may simultaneously analyze the optical angular difference and the absorption energy difference between the light 110 emitted from the light source 102 and the light 110*g*, 110*h* transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball). In addition, since the glucose monitoring function is integrated to the portable mobile device 1100, it is convenient in utilization. Moreover, telemedicine care may be provided by using the program or network of the portable mobile device 1100 to connect to the cloud.

Figure 12:
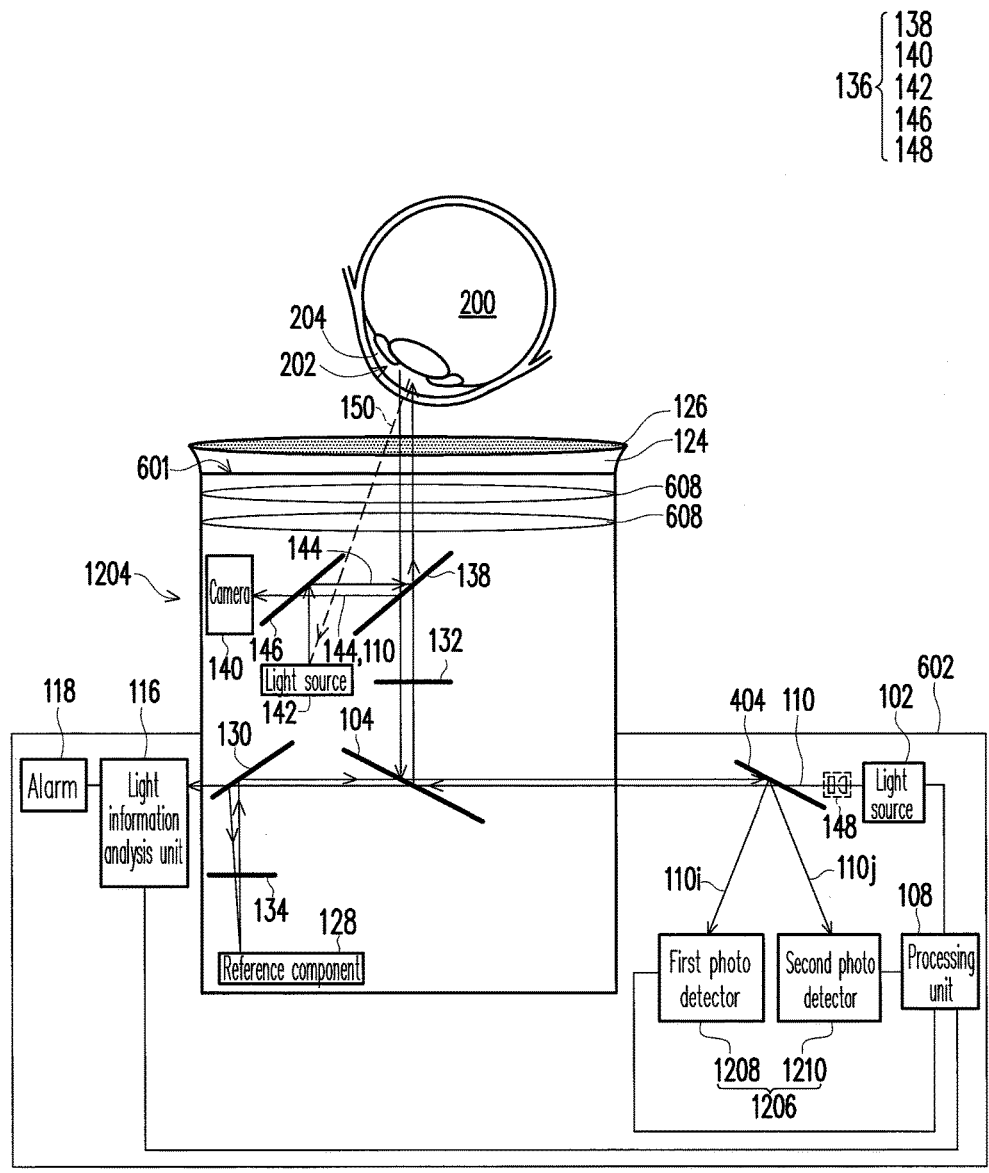
FIG. 12 is a schematic diagram illustrating a portable mobile device with a non-invasive glucose monitoring function in accordance with a twelfth exemplary embodiment.

FIG. 12 is a schematic diagram illustrating a portable mobile device with a non-invasive glucose monitoring function in accordance with a twelfth exemplary embodiment.

Referring to FIG. 7 and FIG. 12, a difference between a portable mobile device 1200 of the twelfth exemplary embodiment and the portable mobile device 700 of the seventh exemplary embodiment is that, in the portable mobile device 1200, the light 110 may generate two rays of light 110*i*, 110*j* after passed through the beam splitter 404. In addition, a set of photo detectors 1206 of the portable mobile device 1200 comprises a first photo detector 1208 and a second photo detector 1210, and the first photo detector 1208 and the second photo detector 1210 are located at a same side of the beam splitter 404. In the present exemplary embodiment, the first photo detector 1208 and the second photo detector 1210 are, for example, located at the side of the beam splitter 404 where the light 110 is reflect from, and are respectively used to measure two rays of light 110*i*, 110*j* generated by reflecting the light 110 through the beam splitter 404. Wherein, one of the first photo detector 1208 and the second photo detector 1210 is, for example, the optical angular measuring device for measuring the optical angular information, and another of the first photo detector 1208 and the second photo detector 1210 is, for example, the measuring device for measuring the absorption energy information. In another exemplary embodiment, the first photo detector 1208 and the second photo detector 1210 may also comprise the optical angular measuring device and the energy measuring device, respectively. The first photo detector 1208 and the second photo detector 1210 are, for example, coupled to the processing unit 108, but the discourse is not limited thereto. Compositions, coupling relations and functions of the other components of the portable mobile device 1200 of the twelfth exemplary embodiment are similar to that of the portable mobile device 700 of the seventh exemplary embodiment, and the similar components in the twelfth exemplary embodiment and in the seventh exemplary embodiment are with similar compositions; furthermore, the method for glucose monitoring may be referred to the fourth exemplary embodiment, so that detailed descriptions thereof are not repeated.

In another example embodiment, the first photo detector 1208 and the second photo detector 1210 may also located at the side of the beam splitter 404 where the light 110 passes there through, and are respectively used to measure light 110*i*, 110*j* generated by the light 110 after passed through the beam splitter 404.

Similarly, the portable mobile device 1200 of the twelfth exemplary embodiment may simultaneously analyze the optical angular difference and the absorption energy difference between the light 110 emitted from the light source 102 and the light 110*i*, 110*g* transmitted to the set of photo detectors 1206, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball). In addition, since the glucose monitoring function is integrated to the portable mobile device 1200, it is convenient in utilization. Moreover, telemedicine care may be provided by using the program or network of the portable mobile device 1000 to connect to the cloud for using the real-time blood glucose data to remind or control medication and to directly inform the medical unit to perform first aid in case of emergency situation.

Figure 13:
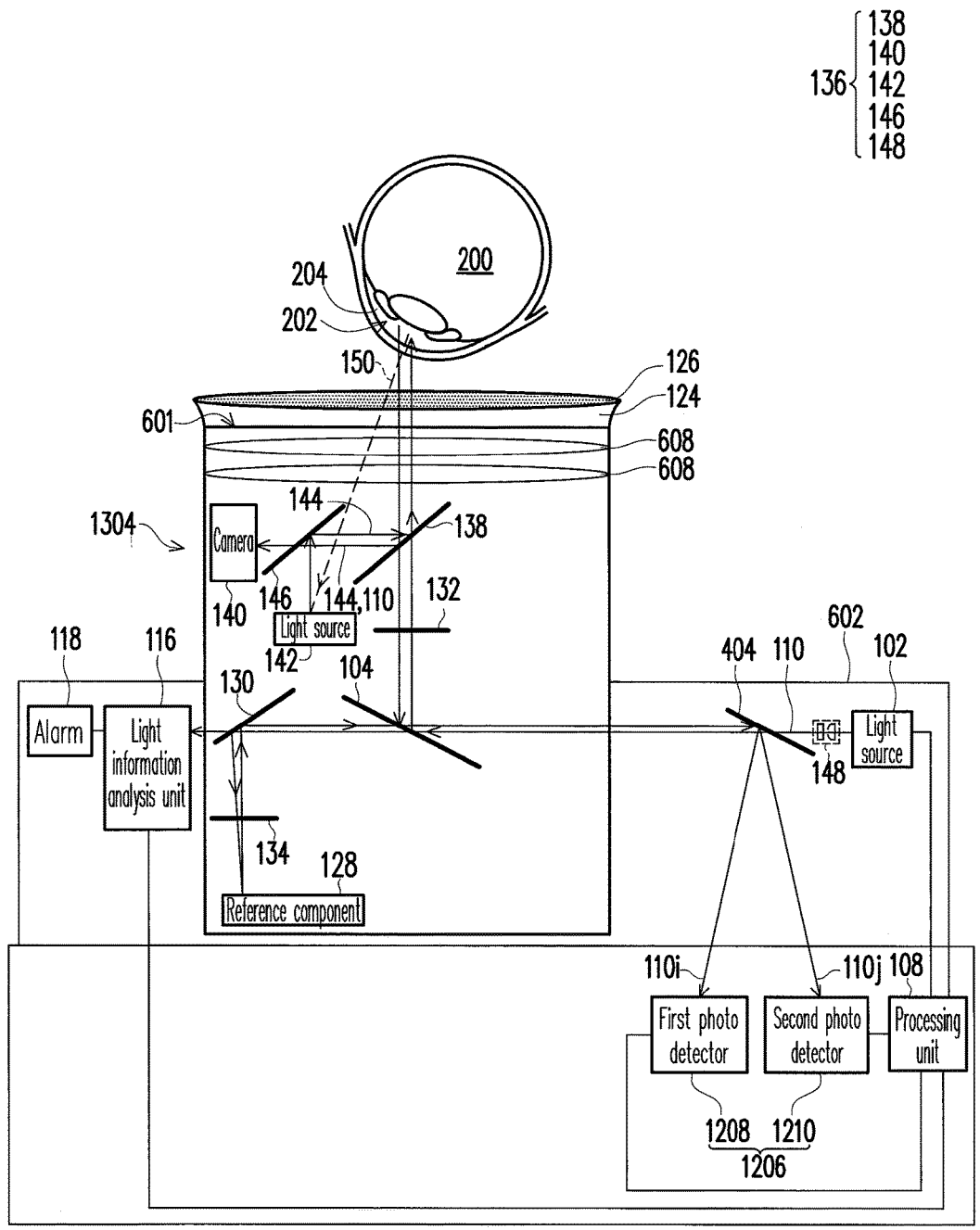
FIG. 13 is a schematic diagram illustrating a portable mobile device with a non-invasive glucose monitoring function in accordance with a thirteenth exemplary embodiment.

FIG. 13 is a schematic diagram illustrating a portable mobile device with a non-invasive glucose monitoring function in accordance with a thirteenth exemplary embodiment.

Referring to FIG. 12 and FIG. 13, a difference between a portable mobile device 1300 of the thirteenth exemplary embodiment and the portable mobile device 1200 of the twelfth exemplary embodiment is that the composition of an optical kit 1304 of the thirteenth exemplary embodiment is different from the composition of an optical kit 1204 of the twelfth exemplary embodiment. The optical kit 1304 is externally attached and disposed on the device body 602, and the optical kit 1304 other than comprises the beam splitter 104 and the lens set 608, also comprises the light source 102 and the beam splitter 404. In addition, the optical kit 904 may further selectively comprise the light information analysis unit 116 and the alarm 118. Compositions, coupling relations and functions of the other components of the portable mobile device 1300 of the thirteenth exemplary embodiment are similar to that of the portable mobile device 1200 of the twelfth exemplary embodiment, and the similar components in the thirteenth exemplary embodiment and in the twelfth exemplary embodiment are with similar compositions; furthermore, the method for glucose monitoring may be referred to the twelfth exemplary embodiment, so that detailed descriptions thereof are not repeated.

Similarly, the portable mobile device 1300 of the thirteenth exemplary embodiment may simultaneously analyze the optical angular difference and the absorption energy difference between the light 110 emitted from the light source 102 and the light 110*i*, 110*j* transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read, through this corresponding relationship, by using the apparatus for non-invasive glucose monitoring of the disclosure to detect the glucose information (e.g., concentration of glucose) in the eyeball (e.g., aqueous humor within the eyeball). In addition, since the glucose monitoring function is integrated to the portable mobile device 1300, it is convenient in utilization. Moreover, telemedicine care may be provided by using the program or network of the portable mobile device 1300 to connect to the cloud.

In addition, although the apparatus for non-invasive glucose monitoring used in the application of portable mobile device described the sixth to the thirteenth exemplary embodiments are taken as examples for the descriptions, but the disclosure is not limited thereto. One of ordinary skill in the art would able to refer to the portable mobile device with a non-invasive glucose monitoring function disclosed in the sixth to the thirteenth exemplary embodiment to combine the concept of the portable mobile device with a non-invasive glucose monitoring function with the various implementations of the first to the fourth exemplary embodiments, so as to produce a diversified portable mobile device with a non-invasive glucose monitoring function.

Moreover, although the first to the thirteenth exemplary embodiments use the examples of measuring a single eye for the descriptions, but the disclosure is not limited thereto. One of ordinary skill in the art would be able to know the method for applying the contents of the present disclosure to both two eyes according the aforementioned exemplary embodiments.

Figure 14:
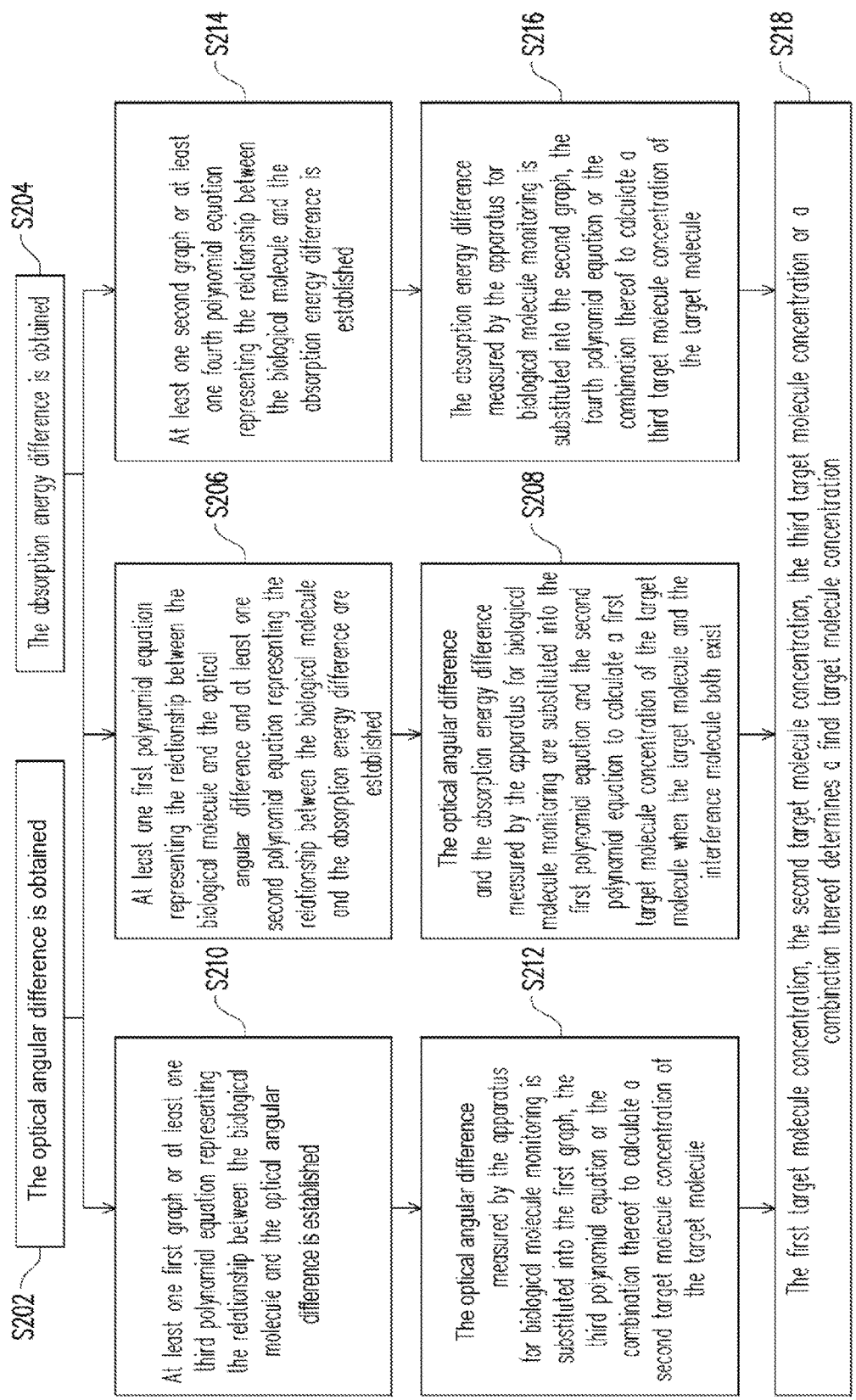
FIG. 14 is a schematic diagram illustrating a method for analyzing biological molecule in accordance with a fourteenth exemplary embodiment.

FIG. 14 is a schematic diagram illustrating a method for analyzing biological molecule in accordance with a fourteenth exemplary embodiment.

The method for analyzing biological molecule in the present exemplary embodiment, for example, performs analyzing through the processing unit of an apparatus for biological molecule monitoring. The biological molecule, such as glucose, cholesterol, uric acid, water, lactic acid, urea, ascorbic acid or a combination thereof is analyzed. The apparatus for biological molecule monitoring, for example, is at least one of the apparatus for non-invasive glucose monitoring described in the first to the fourth exemplary embodiments and the portable mobile device with the non-invasive glucose monitoring function described in the sixth to the thirteenth exemplary embodiments.

Referring to FIG. 14, step S202 may be performed to obtain the optical angular difference. A method for obtaining the optical angular difference comprises the following steps. Firstly, a portion of a plurality of optical angular difference values that exceeded an acceptable variation range measured by the apparatus for biological molecule monitoring is discarded. Then, at least one mathematical statistical method is used to calculate the optical angular difference values. Wherein, the mathematical statistical method is, for example, a least square error regression analysis method. The acceptable variation range is, for example, the range represented by the following listed mathematical formulas.

The acceptable variation range for the optical angular difference=the arithmetic mean of the optical angular difference values×(1±15%).

In addition, step S204 may be performed to obtain the absorption energy difference. A method for obtaining the absorption energy difference comprises the following steps. Firstly, a portion of a plurality of absorption energy difference values that exceeded the acceptable variation range measured by the apparatus for biological molecule monitoring is discarded. Then, at least one mathematical statistical method is used to calculate the absorption energy difference values. Wherein, the mathematical statistical method is, for example, a least square error regression analysis method. The acceptable variation range is, for example, the range represented by the following listed mathematical formulas.

The acceptable variation range for the absorption energy difference=the arithmetic mean of the absorption energy difference values×(1±15%).

Step S206 is performed to establish at least one first polynomial equation representing the relationship between the biological molecule and the optical angular difference, and at least one second polynomial equation representing the relationship between the biological molecule and the absorption energy difference. Wherein, the biological molecule comprises a target molecule and at least one interference molecule, and a plurality of variables of the first polynomial equation and the second polynomial equation respectively comprise the target molecule concentration and the interference molecule concentration variables.

The first polynomial equation is, for example, established from a plurality of biological molecule concentration values and a plurality of corresponding optical angular difference values stored in a database. The second polynomial equation is, for example, established from a plurality of biological molecule concentration values and a plurality of corresponding absorption energy difference values stored in the database. Wherein, samples with a plurality of biological molecule concentration values stored in the database comprises a plurality of live samples or a plurality of standard samples.

In addition, the steps of establishing the first polynomial equation and the second polynomial equation further comprise distinguishing between a plurality of optical angular difference ranges and a plurality of absorption energy difference ranges, having the first polynomial equation correspondingly used in each of the optical angular difference ranges, and having the second polynomial equation correspondingly used in each of the absorption energy ranges.

For example, when the target molecule is the glucose and the interference molecule is the lactic acid, and when three optical angular difference ranges and three absorption energy difference ranges are distinguished, the selected first polynomial equation and second polynomial equation are shown below, but the disclosure is not limited thereto.

The first polynomial equation corresponded to the first optical angular difference range:

$$\theta_{(glucose\ effect+lactic\ acid\ effect)} = a_1 X_{glucose\ concentration} + b_1 Y_{lactic\ acid\ concentration} + c_1$$

The first polynomial equation corresponded to the second optical angular difference range:

$$\theta_{(glucose\ effect+lactic\ acid\ effect)} = a_1' X_{glucose\ concentration} + b_1' Y_{lactic\ acid\ concentration} + c_1'$$

The first polynomial equation corresponded to the third optical angular difference range:

$$\theta_{(glucose\ effect+lactic\ acid\ effect)} = a_1'' X_{glucose\ concentration} + b_1'' Y_{lactic\ acid\ concentration} + c_1''$$

wherein, $\theta_{(glucose\ effect+lactic\ acid\ effect)}$ is the optical angular difference, $X_{glucose}$ concentration is the target molecule concentration variable, $Y_{lactic\ acid\ concentration}$ is the interference molecule concentration variable, $a_1$, $a_1'$, $a_1''$, $b_1$, $b_1'$, $b_1''$, $c_1$, $c_1'$ and $c_1''$ are the known coefficients.

The second polynomial equation corresponded to the first absorption energy difference range:

$$P_{(glucose\ effect+lactic\ acid\ effect)} = a_2 X_{glucose\ concentration} + b_2 Y_{lactic\ acid\ concentration} + c_2$$

The second polynomial equation corresponded to the second absorption energy difference range:

$$P_{(glucose\ effect+lactic\ acid\ effect)} = a_2' X_{glucose\ concentration} + b_2' Y_{lactic\ acid\ concentration} + c_2'$$

The second polynomial equation corresponded to the third absorption energy difference range:

$$P_{(glucose\ effect+lactic\ acid\ effect)} = a_2'' X_{glucose\ concentration} + b_2'' Y_{lactic\ acid\ concentration} + c_2''$$

wherein, $P_{(glucose\ effect+lactic\ acid\ effect)}$ is the absorption energy difference, $X_{glucose\ concentration}$ is the target molecule concentration variable, $Y_{lactic\ acid\ concentration}$ is the interference molecule concentration variable, $a_2$, $a_2'$, $a_2''$, $b_2$, $b_2'$, $b_2''$, $c_2$, $c_2'$ and $c_2''$ are the known coefficients.

Step S208 is performed, by which the optical angular difference and the absorption energy difference measured by the apparatus for biological molecule monitoring are substituted into the first polynomial equation and the second polynomial equation to calculate a first target molecule concentration of the target molecule which simultaneously exists in the target molecule and the interference molecule. A method for calculating the first target molecule concentration is, for example, solving the simultaneous equations of the first polynomial equation and the second polynomial equation. During the process of performing step S208, the optical angular difference and the absorption energy difference are analyzed by controlling the change factor, in order to obtain the first target molecule concentration. Wherein, the change factor comprises a light emitting frequency, a light energy intensity, a length of turn-on time of the light, a length of turn-off time of the light, an opto-element offset, or a combination thereof.

In addition, steps S210, S212, S214, S216, S218, or a combination thereof may be performed selectively.

In step S210, at least one first graph or at least one third polynomial equation representing the relationship between the biological molecule and the optical angular difference is established. Wherein, the variable of the third polynomial equation comprises the target molecule concentration variable.

The first graph and the third polynomial equation, for example, are established from the biological molecule concentration values stored in the database and the corresponding optical angular difference values. Wherein, the samples of the plurality of biological molecule concentration values stored in the database comprise a plurality of live samples or a plurality of standard samples.

In addition, the steps of establishing the first graph or the third polynomial equation further comprise distinguishing a plurality of optical angular difference ranges, having the first graph, the third polynomial equation, or the combination thereof correspondingly used in each of the optical angular difference ranges.

For example, when the target molecule is the glucose and three optical angular difference ranges are distinguished, the selected third polynomial equation is shown below, but the disclosure is not limited thereto.

The third polynomial equation corresponded to the first optical angular difference range:

$$\theta_{(glucose\ effect)} = a_3 X_{glucose\ concentration} + c_3$$

The third polynomial equation corresponded to the second optical angular difference range:

$$\theta_{(glucose\ effect)} = a_3' X_{glucose\ concentration} + c_3'$$

The third polynomial equation corresponded to the third optical rotatory distribution angular difference range:

$$\theta_{(glucose\ effect)} = a_3'' X_{glucose\ concentration} + c_3''$$

wherein, $\theta_{(glucose\ effect)}$ is the optical angular difference, $X_{glucose\ concentration}$ is the target molecule concentration variable, $a_3$, $a_3'$, $a_3''$, $c_3$, $c_3'$ and $c_3''$ are the known coefficients.

In step S212, the optical angular difference measured by the apparatus for biological molecule monitoring is substituted into the first graph, the third polynomial equation or the combination thereof to calculate a second target molecule concentration of the target molecule. During the process of performing step S212, the optical angular difference is analyzed by controlling the change factor, in order to obtain the second target molecule concentration. Wherein, the change factor comprises the light emitting frequency, the light energy intensity, the length of turn-on time of the light, the length of turn-off time of the light, the opto-element offset, or the combination thereof.

In step S214, at least one second graph or at least one fourth polynomial equation representing the relationship between the biological molecule and the absorption energy difference is established. Wherein, the variable of the fourth polynomial equation comprises the target molecule concentration variable.

The second graph and the fourth polynomial equation, for example, are established from the biological molecule concentration values and the corresponding absorption energy difference values stored in the database. Wherein, samples with a plurality of biological molecule concentration stored in the database comprise a plurality of live samples or a plurality of standard samples.

In addition, the steps of establishing the second graph or the fourth polynomial equation further comprise distinguishing a plurality of absorption energy difference ranges, having the second graph, the fourth polynomial equation, or the combination thereof correspondingly used in each of the absorption energy difference ranges.

For example, when the target molecule is the glucose and three absorption energy difference ranges are distinguished, the selected fourth polynomial equation is shown below, but the disclosure is not limited thereto.

The fourth polynomial equation corresponded to the first absorption energy difference range:

$$P_{(glucose\ effect)} = a_4 X_{glucose\ concentration} + c_4$$

The fourth polynomial equation corresponded to the second absorption energy difference range:

$$P_{(glucose\ effect)} = a_4' X_{glucose\ concentration} + c_4'$$

The fourth polynomial equation corresponded to the third absorption energy difference range:

$$P_{(glucose\ effect)} = a_4'' X_{glucose\ concentration} + c_4''$$

wherein, $P_{(glucose\ effect)}$ is the absorption energy difference, $X_{glucose\ concentration}$ is the target molecule concentration variable, $a_4$, $a_4'$, $a_4''$, $c_4$, $c_4'$ and $c_4''$ are the known coefficients.

In step S216, the absorption energy difference measured by the apparatus for biological molecule monitoring is substituted into the second graph, the fourth polynomial equation or the combination thereof to calculate a third target molecule concentration of the target molecule. During the process of performing step S216, the absorption energy difference is analyzed by controlling the change factor, in order to obtain the third target molecule concentration. Wherein, the change factor comprises the light emitting frequency, the light energy intensity, the length of turn-on time of the light, the length of turn-off time of the light, the opto-element offset, or the combination thereof.

In step S218, the first target molecule concentration, the second target molecule concentration, the third target molecule concentration or a combination thereof determines a final target molecule concentration. In another embodiment, when the step S218 is not performed, the first target molecule concentration obtained through the step S208 may be used as the final target molecule concentration.

According to the fourteenth embodiment, the analysis method of the above-mentioned biological molecule may obtain the target molecule concentration, which simultaneously exists in the target molecule and the interference molecule through the optical angular difference values and the absorption energy difference values; therefore, a more accurate concentration of target molecule may be obtained.

EXAMPLES

A relationship formula for representing energy absorptions of glucose and other substances, such as urea, water, vitamins and so forth, in the aqueous humor is as described in equation (1).

$$A_{total} = A_{glucose} + [A_{vitamin} + A_i + \ldots] \quad (1)$$
$$= \varepsilon_1 b c_1 + [\varepsilon_2 b c_2 + \varepsilon_3 b c_3 + \ldots]$$

A relationship formula for representing optical angular angles of the glucose and the other substances, such as urea, water, vitamins and so forth, in the aqueous humor is as described in equation (2).

$$\theta_{total} = \theta_{glucose} + [\theta_{vitamin} + \theta_i + \ldots] \quad (2)$$
$$= \phi_1 b c_1 + [\phi_2 b c_2 + \phi_3 b c_3 + \ldots]$$

$A_{total}$: the total energy absorption of the aqueous humor detected by the biological molecule monitoring device;

$A_{glucose}$, $A_{vitamin}$, $A_i$: respectively represent the energy absorptions of the glucose, the vitamin and other different compositions in the aqueous humor;

$\theta_{total}$: the total optical angular angle of the aqueous humor detected by the biological molecule monitoring device;

$\theta_{glucose}$, $\theta_{vitamin}$, $\theta_i$: respectively represent the optical angular angles generated by the glucose, the vitamin and other different compositions in the aqueous humor;

$\varepsilon_1$, $\varepsilon_2$, $\varepsilon_3$ ... : the molar absorptivity coefficient of each substance, which typically adopts $M^{-1}\ cm^{-1}$ as unit;

b: the optical path, which typically adopts $cm^{-1}$ as unit;

$c_1$, $c_2$, $c_3$ ... : the molar concentration of each substance, which typically adopts M as unit;

$\phi_1$, $\phi_2$, $\phi_3$ ... : the theoretical optical angular angle coefficient of each substance, which typically adopts $M^{-1}\ cm^{-1}$ as unit.

Assuming there are two types of components included in the aqueous humor, wherein one of the components is glucose, such that the energy absorption of the glucose is $A_{glucose}$, while the other one of the component is vitamin, such that the energy absorption of the vitamin is $A_{vitamin}$, then the original equations (1) and (2) may be simplified as:

$$A_{total} = A_1 \times c_{glucose} + A_2 \times c_{vitamin} + \text{constant } C_1 \quad (3)$$

$$\theta_{total} = B_1 \times c_{glucose} + B_2 \times c_{vitamin} + \text{constant } C_2 \quad (4)$$

wherein, $A_1$ and $A_2$ ... respectively represent the proportions of the energy absorptions of the different compositions in the aqueous humor, and $B_1$ and $B_2$ ... respectively represent the proportions of the optical angular angles generated by the different compositions in the aqueous humor.

To simplify the description, assuming there are only an unknown concentration of glucose and an unknown concentration of vitamin included in the aqueous humor, and a length of the optical path is b, then $A_1$ represents the ratio in percentage of the energy absorption of the glucose to the total energy absorption on a fixed optical path b;

$A_2$ represents the ratio in percentage of the energy absorption of the vitamin to the total energy absorption on a fixed optical path b;

$B_1$ represents the ratio in percentage of the optical angular angle of the glucose to the total optical angular angle on a fixed optical path b;

$B_2$ represents the ratio in percentage of the optical angular angle of the vitamin to the total optical angular angle on a fixed optical path b;

$c_{glucose}$: the molar concentration of the glucose;

$c_{vitamin}$: the molar concentration of the vitamin.

By substituting the measured values in to the equations (3) and (4), the equations (3) and (4) may be modified into equations (5) and (6).

$$7.5 = 0.1 \times c_{glucose} + 0.2 \times c_{vitamin} + 0.5 \quad (5)$$

$$46.1 = 0.9 \times c_{glucose} + 0.1 \times c_{vitamin} + 0.1 \quad (6)$$

In order to reduce an influence of noise (e.g., temperature . . . ), calculations of the values of the absorption concentration and the optical angular angle of a single analyte are calibrated according to the laser controlled by the feedback mechanism. Finally, after being calibrated by the feedback mechanism, each of the values of the absorption concentration or the optical angular angle is detected; and through the equations (5) and (6), the concentration of the glucose is calculated to be 50 mg/dL and the concentration of the vitamin is calculated to be 10 mg/dL.

Accordingly, the concentrations of two different substances may be determined through the above-described methods. If in simultaneous collocation with the absorption and optical angular angle characteristics of different interfering substances, the present logic algorithm may determine the conditions of the glucose and at least one type of mixture in the aqueous humor. Moreover, the values of the absorption concentration and the optical angular angle calculated according to the feedback mechanism may also be avoided from the environmental noise interference.

In summary, the above embodiments at least include the following features. The apparatus for non-invasive glucose monitoring provided by the aforementioned exemplary embodiments may be used to measure the glucose information accurately (e.g., concentration of glucose) of the measuring object, and since the concentration of glucose in the eyeball (e.g., aqueous humor within the eyeball) has a relationship with the concentration of blood glucose, the blood glucose information (e.g., concentration of blood glucose) may be read, through this corresponding relationship, by using the apparatus for non-invasive glucose monitoring of the disclosure to detect the glucose information (e.g., concentration of glucose) in the eyeball (e.g., aqueous humor within the eyeball). The portable mobile device with a non-invasive glucose monitoring function provided by the aforementioned exemplary embodiments may be miniaturized in applications, so as to improve utilization convenience. Utilization environments of the portable mobile device with a non-invasive glucose monitoring function provided by the aforementioned exemplary embodiments have no special restriction, thus may be used indoors and outdoors. The concentration of blood glucose of the measuring object may be continuously obtained in real time according to the method for non-invasive glucose monitoring provided by the aforementioned exemplary embodiment. The analysis method for the biological molecule provided by the aforementioned exemplary embodiment may obtain the target molecule concentration which simultaneously exists in the target molecule and the interference molecule, through the optical angular difference values and the absorption energy difference values; therefore, a more accurate concentration of target molecule may be obtained. In addition, when the apparatus for non-invasive glucose monitoring provided in the aforementioned exemplary embodiment has the reference component, the light intensity difference caused by the environmental impact may be avoided, so as to obtain the more accurate glucose information, thereby enhancing the accuracy of the blood glucose information (e.g., concentration of blood glucose). Moreover, when the apparatus for non-invasive glucose monitoring provided in the aforementioned exemplary embodiment has the eye positioning device, the measurement error due to the light not being fell on the accurate measuring position of the eyeball may be avoided, so that the apparatus for non-invasive glucose monitoring may obtain the more precise glucose information, thereby enhancing the accuracy of the blood glucose information (e.g., concentration of blood glucose).

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An apparatus for non-invasive glucose monitoring, comprising:
   at least one light source, emitting at least one ray of light;
   a first beam splitter with a focusing function, leading the light emitted from the light source into an eyeball and focusing on the eyeball through the first beam splitter;
   a polarizer;
   a set of light sensing elements, wherein the light sensing elements simultaneously measure at least two properties of the light reflected from the eyeball transmitted onto the set of light sensing elements, wherein one of the at least two properties measured comprises an absorption energy information of the reflected light transmitted by the first beam splitter, and another of the at least two properties measured comprises an optical angular information of the polarized light transmitted through the polarizer;
   a reference component, wherein the reference component receives the reflected light from the first beam splitter, wherein the reflected light is transmitted by the first beam splitter to the set of light sensing elements, wherein the light emitted from the light source is directed to the eyeball through the first beam splitter, reflected by the eyeball, and then transmitted to the set of light sensing elements by the first beam splitter to form a first optical path, and the light emitted from the light source, transmitted to the reference component by the first beam splitter is reflected by the reference component, and then transmitted to the set of light sensing elements by the first beam splitter to form a second optical path, and wherein the at least two properties of the light transmitted on the first optical path and the at least two properties of the light the second optical path are measured in sequence; and
   a processing unit, wherein the processing unit obtains a glucose information by receiving and analyzing the optical angular information and the absorption energy information by at least two polynomial equations, wherein the at least two polynomial equations comprises a first polynomial equation and a second polynomial equation, the first polynomial equation represents relationship between a biological molecule information and the optical angular difference, and the second polynomial equation represents relationship between the biological molecule information and the absorption energy difference, the biological molecule information comprises the glucose information.

2. The apparatus for non-invasive glucose monitoring according to claim 1, wherein the light reflected by the reference component on the second optical path has a characteristic intensity.

3. The apparatus for non-invasive glucose monitoring according to claim 2, wherein the set of light sensing elements obtains a reference intensity of the light reflected by the reference component from the second optical path when performing an actual measurement.

4. The apparatus for non-invasive glucose monitoring according to claim 3, wherein the processing unit calculates an optical angular distribution difference and an absorption energy difference between the light emitted from the light source and the light transmitted to the set of light sensing elements through the first optical path, and a light intensity difference caused by environmental impact is avoided by comparing the characteristic intensity with the reference intensity, a biological molecule information of a biological molecule is calculated, the biological molecule at least comprises a glucose, the processing unit calculates the glucose information through the biological molecule information, and a blood glucose information is read since the glucose information and the blood glucose information have a corresponding relationship.

5. The apparatus for non-invasive glucose monitoring according to claim 1, wherein the reference component comprises a reference sheet or a reference solution.

6. The apparatus for non-invasive glucose monitoring according to claim 1, wherein the reference component comprises a light absorbing material, a light reflective material or a solution.

7. The apparatus for non-invasive glucose monitoring according to claim 1 further comprising a light information analysis unit that detects a light information of the light from the first beam splitter before the light is directed into the eyeball, and then transmits the light information to the processing unit, an alarm or a light source control unit performs a feedback control with an optical characteristic of the light.

8. The apparatus for non-invasive glucose monitoring according to claim 7, wherein the light information analysis unit comprises at least one of an optical power meter and an optical sensor, the light information detected by the optical power meter is an energy information, and the light information detected by the optical sensor is at least one of the energy information and a position information.

9. The apparatus for non-invasive glucose monitoring according to claim 7 further comprising a second beam splitter respectively transmitting the light from the first beam splitter to the reference component and the light information analysis unit.

10. The apparatus for non-invasive glucose monitoring according to claim 7 further comprising a first shutter disposed on the first optical path between the first beam splitter and the eyeball.

11. The apparatus for non-invasive glucose monitoring according to claim 7 further comprising a second shutter disposed on the second optical path between the first beam splitter and the reference component.

12. The apparatus for non-invasive glucose monitoring according to claim 1, wherein a wavelength of the light source comprises a glucose absorbable wavelength.

13. The apparatus for non-invasive glucose monitoring according to claim 1, wherein a wavelength of the light source comprises a wavelength of an infrared light.

14. The apparatus for non-invasive glucose monitoring according to claim 1, wherein the light comprises a linear polarized light, a circular polarized light, an elliptical polarized light or a partial polarized light.

15. The apparatus for non-invasive glucose monitoring according to claim 1, wherein the first beam splitter directs the light to focus onto an anterior chamber of the eyeball, and the light reflected from the eyeball comprises a reflected light from an aqueous humor.

16. The apparatus for non-invasive glucose monitoring according to claim 1, wherein the first beam splitter comprises an optical film, an optical lens, an optical grating, a diffractive optic element or a combination of any the above elements.

17. The apparatus for non-invasive glucose monitoring according to claim 1, wherein the set of light sensing elements comprises an optical-angular measuring device and an energy measuring device, which respectively measure the light reflected from the eyeball and then reflected by or passed through the first beam splitter.

18. The apparatus for non-invasive glucose monitoring according to claim 1, further comprising a third beam splitter configured to transmit the light reflected from the eyeball and then transmitted through the first beam splitter to the set of light sensing elements.

19. The apparatus for non-invasive glucose monitoring according to claim 18, wherein the light reflected by or passed through the third beam splitter is respectively measured by one of the set of light sensing elements, and passed through the polarizer and measured by another of the set of light sensing elements.

20. The apparatus for non-invasive glucose monitoring according to claim 1, further comprising an eye-alignment positioning device that is configured to align a sight of an eye with the eye-alignment positioning device and determines a measuring position of the eyeball.

* * * * *